US007244837B2

(12) United States Patent
Malutan et al.

(10) Patent No.: US 7,244,837 B2
(45) Date of Patent: *Jul. 17, 2007

(54) INSECT MONOAMINE TRANSPORTER AND METHODS OF USE THEREOF

(75) Inventors: Tabita Malutan, London (CA); Cameron Donly, London (CA); Stanley Caveney, London (CA)

(73) Assignees: The University of Western Ontario, Ontario (CA); Her Majesty the Queen in right of Canada as represented by the Minister, the Dept of Agriculture + Agrifood Canada, Ontario (CA)

( * ) Notice: Subject to any disclaimer, the term of this patent is extended or adjusted under 35 U.S.C. 154(b) by 543 days.

This patent is subject to a terminal disclaimer.

(21) Appl. No.: 10/756,533

(22) Filed: Jan. 12, 2004

(65) Prior Publication Data

US 2004/0214279 A1    Oct. 28, 2004

Related U.S. Application Data

(63) Continuation-in-part of application No. 09/587,811, filed on Jun. 6, 2000, now Pat. No. 6,677,443.

(60) Provisional application No. 60/137,929, filed on Jun. 7, 1999.

(51) Int. Cl.
*C07K 1/00* (2006.01)
*C07H 21/04* (2006.01)
*C12N 1/20* (2006.01)
*C12P 21/06* (2006.01)
*G01N 33/566* (2006.01)

(52) U.S. Cl. ............... 536/23.5; 530/300; 530/350; 530/858; 536/23.1; 435/6; 435/7.21; 435/69.1; 435/252.3; 435/320.1; 435/325; 436/501

(58) Field of Classification Search ............... None
See application file for complete search history.

(56) References Cited

U.S. PATENT DOCUMENTS 6,677,443 B1 * 1/2004 Malutan et al. ............ 536/23.5

FOREIGN PATENT DOCUMENTS

WO    9300811    1/1993
WO    9308261    4/1993

OTHER PUBLICATIONS

Duerr et al. (1999) The cat-1 Gene of Caenorhabditis elegans Encodes a Vesicular Monoamine Transporter Required for Specific Monoamine-Dependent Behaviors. Journal of Neuroscience 19:72-84.

Kitayama and Dohi, (1996) Cellular and Molecular Aspects of Monoamine Neurotransmitter Transporters. *Jpn J. Pharmacol.* 72: 195-208.

Richard H. Osborne. (1996) Insect Neurotransmission: Neurotransmitters and Their Receptors. *Pharmacol. Ther.* 69: 117-142.

Thompson et al. (1994) Clustal W: improving the sensitivity of progressive multiple sequence alignment through sequence weighting, position-specific gap penalties and weight matrix choice. *Nucleic Acids Res.* 22:4673-4680.

Kitts et al. (1993) A Method for Producing Recombinant Baculovirus Expression Vectors at High Frequency. *BioTechniques*, 14:810-817.

Nathanson et al. (1993) Cocaine as a naturally occurring insecticide. Proc. Natl. Acad. Sci. USA 90:9645-9648.

Shafqat et al. (1993) Molecular Characterization of Neurotransmitter Transporters. *Mol. Endocrinol.* 7:1517-1529.

Alexander et al. (1992) Altering the antigenicity of proteins. Proc. Natl. Acad. Sci. 89;3352-3356.

Bowie et al. (1990) Deciphering the Message in Protein Sequences: Tolerance to Amino Acid Substitutions. Science 247:1306-1310.

Saudou et al. (1990) Cloning and characterization of a Drosophila tyramine receptor. The EMBO Journal 9:3611-3617.

Kaufman et al. (1989) Drosophila P Element Transposase Recognizes Internal P Element DNA Sequences. *Cell* 59:359-371.

Luckow et al. (1988) Trends in the development of baculovirus expression vectors. *Bio/Technology* 6:47-55.

Lois K. Miller (1988) Baculovirus as gene expression vectors. *Ann. Rev. Microbiol.* 42:177-199.

Marilyn Kozak (1987) An analysis of 5'-noncoding sequence from 699 vertebrate messanger RNAs. *Nucleic Acids Res.* 15:8125-8132.

Stellar et al. (1985) A transposable P vector that confers selectable G418 resistance to Drosophila larvae. *EMBO J.*, 4:167-171.

Cheng et al. (1973) Relationship between the inhibition constant ($K_1$) and the concentration of inhibitor which causes 50 per cent inhibition ($I_{50}$) of an enzymatic reaction. *Biochemical Pharmacology* 22:3099-3108.

\* cited by examiner

*Primary Examiner*—Janet L. Andres
*Assistant Examiner*—Michael Brannock
(74) *Attorney, Agent, or Firm*—Baker Botts LLP

(57) ABSTRACT

The present invention is directed to a lepidopteran octopamine/tyramine transporter. Nucleic acids encoding the transporter, and vectors and host cells comprising the nucleic acids are provided. The invention further provides a recombinant octopamine/tyramine transporter, kits and compositions comprising the transporter, and methods of identifying agents that mediate the activity of the transporter.

7 Claims, 8 Drawing Sheets

FIG. 1

```
ggcacgaggtcgcctgagacgcacggtcgcagcccccgaaaatacttcgcaagttaccgagtgatcacactgagtgcctc  -304
tcaaacttccaaagcaaatacaacggaacttattgagaatttattgg(aa)tggcgagcaggcacgggtagcgcagcgggcg  -224
gc[atg]cgggc[atg]cccgtgctcgggaacagcgtcggagccggcgaactgcgcgacaccagccgcgaggcgagcaacagg  -144
tcgtcaagcagcggctcccggcgcggctcctccccgcaccacgcacaggaccatgagacgtgtgacgcgaccgtccacaa   -64
gcctgacctgacgaggacgcggcccaccagctatgaccgggagtaccacgataaggtccccac[ATG]CGACGTTAAGCG    16
                                                                 M  A  T  L  S    [5]
GTACTGGTGTGGTGACCCACACAGCTCCGTCTTACGAGGAGCAACGCGCGAACCCCGCGCTGCTCAGCCGCGGCGCCAGC    96
 G  T  G  V  V  T  H  T  A  P  S  Y  E  E  Q  R  A  N  P  A  L  L  S  R  G  A  S   [32]
GGCACGCCCGGCGGCCGCAGCGTCAGGGATGACGGCTACTGCTCAGCTAGCAGCACGCCCAGAGCCTTCGACAACAAATC   176
 G  T  P  G  G  R  S  V  R  D  D  G  Y  C  S  A  S  S  T  P  R  A  F  D  N  K  S   [59]
TACGAAAGGTTCAGTGGTGACCCTGTCCTGTTATAAGAAGGAACCCAAAATACAAATAGAGGAGGAATGCTTCTATAGTG   256
 T  K  G  S  V  V  T  L  S  C  Y  K  K  E  P  K  I  Q  I  E  E  E  C  F  Y  S      [85]
AACCGAATAAACGACTCAGGACGAATAGTATCAAGACTGAGGCTGATGATGGGCGGGAGACGTGGGGCACGGGCGCGGAC   336
 E  P  N  K  R  L  R  T  N  S  I  K  T  E  A  D  D  G  R  E  T  W  G  T  G  A  D   [112]
TTTCTGCTCTCCATCATTGGATTTGCAGTGGATCTCGCCAATGTCTGGCGGTTCCCGTATCTCTGCTACAGGAATGGCGG   416
 F  L  L  S  I  I  G  F  A  V  D  L  A  N  V  W  R  F  P  Y  L  C  Y  R  N  G  G   [139]
TGGTGCATTCCTGATCCCTTACACGTTGATGCTGGTGTTCGGTGCTGTTCCACTATTCTACATGGAGCTTATCCTCGGAC   496
 G  A  F  L  I  P  Y  T  L  M  L  V  F  G  A  V  P  L  F  Y  M  E  L  I  L  G      [165]
AGTACAACCGGCAGGGACCGATCACGCTCTGGAAGATATGCCCGCTCTTCAAAGGTGTGGGGTTCTGCGCGGTGATGGTG   576
 Q  Y  N  R  Q  G  P  I  T  L  W  K  I  C  P  L  F  K  G  V  G  F  C  A  V  M  V   [192]
GCTTTCTACGTCTCCTTCTACTATAACGTCATCATCGGATGGGCGTTCTACTTCCTAGTGTCATCAGCTCGGTCGGAGCT   656
 A  F  Y  V  S  F  Y  Y  N  V  I  I  G  W  A  F  Y  F  L  V  S  S  A  R  S  E  L   [219]
CCCGTGGGTGCACTGCGACAACTCGTGGAACACAGACCAGTGCTGGGACTCCGGCCGGGACAACGCTACCAACAGGACTG   736
 P  W  V  H  C  D  N  S  W  N  T  D  Q  C  W  D  S  G  R  D  N  A  T  N  R  T      [245]
ATGTCCGCTACCAGGGACCGCTGTCGCACTTCACGCCGGCTTCCGAGTTCTTTCATCGAGCTGTCCTTGAGATGCAGAAC   816
 D  V  R  Y  Q  G  P  L  S  H  F  T  P  A  S  E  F  F  H  R  A  V  L  E  M  Q  N   [272]
TCCGAGGGTCTGAATGACTTGGGCTTCCCGAAATGGCAACTGGCGATTTGCTTGGGGCTGGTGTACGTCACTCTCTACCT   896
 S  E  G  L  N  D  L  G  F  P  K  W  Q  L  A  I  C  L  G  L  V  Y  V  T  L  Y  L   [299]
GTCGCTGTTCAAAGGCGTCAAGAGCTCCGGAAAAGTGGTATGGATGACAGCAACGATGCCATACGTGGTGCTCTCCATCC   976
 S  L  F  K  G  V  K  S  S  G  K  V  V  W  M  T  A  T  M  P  Y  V  V  L  S  I      [325]
TCCTTGCTCGAGGACTGCTGCTGCCCGGCGCCACGCGAGGCATCGCCTACTATCTGCAGCCAGAACTCACCAGGCTGAAG  1056
 L  L  A  R  G  L  L  L  P  G  A  T  R  G  I  A  Y  Y  L  Q  P  E  L  T  R  L  K   [352]
GATACACAAGTGTGGGTGGATGCGGCAGTTCAAATCTTCTACTCTGTCGGCGCTGGTTTTGGAGTCCACCTCTCGTACGC  1136
 D  T  Q  V  W  V  D  A  A  V  Q  I  F  Y  S  V  G  A  G  F  G  V  H  L  S  Y  A   [379]
CAGTTACAACACGTTTCACAATAACTGCTACAGAGACTGTTTGGTTACGACGCTGGTCAACTGTTTCACGTCATTTTTCT  1216
 S  Y  N  T  F  H  N  N  C  Y  R  D  C  L  V  T  T  L  V  N  C  F  T  S  F  F      [405]
CCGGATTCGTAATCTTCACATATCTTGGATTCATGTCTCATAAACAAGGCGTACCGATATCGTCAGTGGCCACCGAAGGT  1296
 S  G  F  V  I  F  T  Y  L  G  F  M  S  H  K  Q  G  V  P  I  S  S  V  A  T  E  G   [432]
CCTGGGCTGGTGTTCCAAGTGTATCCCGAGGCCGTGGCCGACCCTACCGGGTGCCAGTCTGTGGGCGATGCTCTTCTTCTT  1376
 P  G  L  V  F  Q  V  Y  P  E  A  V  A  T  L  P  G  A  S  L  W  A  M  L  F  F      [459]
CATGCTCATCATGCTAGGATTGGATTCGGGGATGGGCGGTCTGGAGTGCGTGATCACCGGCTTGCTGGACCAGGCGCGTG  1416
 M  L  I  M  L  G  L  D  S  G  M  G  G  L  E  C  V  I  T  G  L  L  D  Q  A  R      [485]
CGTGTGGTGCCACCTGGCTGCGGCGAGAACATTTCACCCTCATCGTCGTCTGTGTATCATTCTGCGTGGCCTGTATTAAT  1536
 A  C  G  A  T  W  L  R  R  E  H  F  T  L  I  V  V  C  V  S  F  C  V  A  C  I  N   [512]
GTTACACCGGGCGGTATCTACATGTTCCATCTCCTAGACACGTATGCTGCTGGTATCTCGTTGCTCTGCTCCGCGCTGTT  1616
 V  T  P  G  G  I  Y  M  F  H  L  L  D  T  Y  A  A  G  I  S  L  L  C  S  A  L  F   [539]
CGAAGCCGTTGCTGTGTCTTGGTTCTATGGTTTGAAACGGTTTCTGATGACGTGGAGGAGATGCTCGGCTTCCGACCTG  1696
 E  A  V  A  V  S  W  F  Y  G  L  K  R  F  S  D  D  V  E  E  M  L  G  F  R  P      [565]
GTCTGTACTGGAGGATATGCTGGAAGTTCGTCAGTCCCACCTTCATTATTGGTGTGGTGGTATTCGGGCTGCTATACCAG  1776
 G  L  Y  W  R  I  C  W  K  F  V  S  P  T  F  I  I  G  V  V  V  F  G  L  L  Y  Q   [592]
CAGCCTCTCCAGTACCAGCAGTACACGTACCCGCCGTGGGCCGTGGTGCTGGGCTGGGGGCTGGCCTGCTCCTCCATCCT  1856
 Q  P  L  Q  Y  Q  Q  Y  T  Y  P  P  W  A  V  V  L  G  W  G  L  A  C  S  S  I  L   [619]
CATGATCCCAGTCGTCGGTATCTACAAGCTCATCTCCACGCCGGGGACATTCCGTGAGCGCGTGGCTTGCTGTATTTCAC  1936
 M  I  P  V  V  G  I  Y  K  L  I  S  T  P  G  T  F  R  E  R  V  A  C  C  I  S      [645]
CGGAATCTGAGCACGAGGCCATTCGGGGAGGCGCCCCTGTCAGCCGGTTCTCCTGGCGACACTGGCTGTACGT(GTAA)acg  2016
 P  E  S  E  H  E  A  I  R  G  G  A  P  V  S  R  F  S  W  R  H  W  L  Y  V         [670]
aacctttatggctattctggaagattcgaataaagaaggtctatatcttagtcagaaataggcgcttcggagaggaaaaa  2096
gaggggaaaaaaaaaaaaaaaaa                                                            2120
```

FIG 3

Percent Identity

|   | 1 | 2 | 3 | 4 | 5 | 6 | 7 | 8 | 9 |   |   |
|---|---|---|---|---|---|---|---|---|---|---|---|
| 1 |   | 78.2 | 74.3 | 77.7 | 79.7 | 76.8 | 81.5 | 72.1 | 80.2 | 1 | Trichoplusia pOAT |
| 2 | 19.3 |   | 70.9 | 72.7 | 73.9 | 73.4 | 76.8 | 68.9 | 76.6 | 2 | Agriotis pOAT |
| 3 | 28.0 | 29.8 |   | 73.0 | 70.3 | 72.1 | 70.9 | 69.6 | 76.4 | 3 | Bombyx pOAT |
| 4 | 22.6 | 24.5 | 28.6 |   | 77.0 | 77.3 | 76.1 | 71.8 | 75.7 | 4 | Calpodes pOAT |
| 5 | 21.8 | 23.5 | 33.5 | 24.3 |   | 78.6 | 78.2 | 72.5 | 79.1 | 5 | Choristoneura pOAT |
| 6 | 25.4 | 24.4 | 30.9 | 24.1 | 23.4 |   | 75.2 | 75.5 | 79.1 | 6 | Ostrinia pOAT |
| 7 | 18.8 | 19.9 | 31.6 | 23.3 | 22.2 | 25.0 |   | 73.2 | 77.0 | 7 | Lambdina pOAT |
| 8 | 30.7 | 30.6 | 32.5 | 29.4 | 28.5 | 26.3 | 28.5 |   | 73.2 | 8 | Pieris pOAT |
| 9 | 21.0 | 20.6 | 25.9 | 26.8 | 23.1 | 23.2 | 23.2 | 28.4 |   | 9 | Manduca pOAT |
|   | 1 | 2 | 3 | 4 | 5 | 6 | 7 | 8 | 9 |   |   |

Divergence

FIG. 6

Percent Identity

|   | 1 | 2 | 3 | 4 | 5 | 6 | 7 | 8 | 9 |   |   |
|---|---|---|---|---|---|---|---|---|---|---|---|
| 1 |   | 92.7 | 94.0 | 92.7 | 90.7 | 92.0 | 92.0 | 90.0 | 94.7 | 1 | Trichoplusia pOAT |
| 2 | 6.4 |   | 91.3 | 88.7 | 86.0 | 87.3 | 88.0 | 86.7 | 92.0 | 2 | Agriotis pOAT |
| 3 | 6.4 | 7.8 |   | 94.7 | 90.0 | 92.0 | 91.3 | 87.3 | 96.7 | 3 | Bombyx pOAT |
| 4 | 7.8 | 10.9 | 5.6 |   | 93.3 | 93.3 | 90.7 | 89.3 | 95.3 | 4 | Calpodes pOAT |
| 5 | 10.1 | 14.1 | 10.9 | 7.1 |   | 92.7 | 93.3 | 89.3 | 92.0 | 5 | Choristoneura pOAT |
| 6 | 8.6 | 12.5 | 8.6 | 7.1 | 7.8 |   | 91.3 | 90.0 | 94.0 | 6 | Ostrinia pOAT |
| 7 | 7.9 | 11.0 | 8.7 | 9.4 | 6.4 | 8.7 |   | 90.7 | 92.7 | 7 | Lambdina pOAT |
| 8 | 10.9 | 13.3 | 14.1 | 11.7 | 11.7 | 10.9 | 9.4 |   | 88.7 | 8 | Pieris pOAT |
| 9 | 5.6 | 7.1 | 3.5 | 4.9 | 8.6 | 6.4 | 7.1 | 12.5 |   | 9 | Manduca pOAT |
|   | 1 | 2 | 3 | 4 | 5 | 6 | 7 | 8 | 9 |   |   |

Divergence

SEQUENCE LISTING

<160> NUMBER OF SEQ ID NOS: 40

<210> SEQ ID NO 1
<211> LENGTH: 2504
<212> TYPE: DNA
<213> ORGANISM: Trichoplusia ni

<400> SEQUENCE: 1

```
ggcacgaggt cgcctgagac gcacggtcgc agcccccgaa atacttcgc aagttaccga      60
gtgatcacac tgagtgcctc tcaaacttcc aaagcaaata acggaactt attgagaatt     120
tattggtaat ggcgagcagg cacgggtagc gcagcgggcg gcatggcggg catgcccgtg    180
ctcgggaaca gcgtcggagc cggcgaactg cgcgacacca gccgcgaggc gagcaacagg    240
tcgtcaagca gcggctcccg gcgcggctcc tccccgcacc acgcacagga ccatgagacg    300
tgtgacgcga ccgtccacaa gcctgacctg acgaggacgc ggcccaccag ctatgaccgg    360
gagtaccacg ataaggtccc caccatggcg acgttaagcg gtactggtgt ggtgacccac    420
acagctccgt cttacgagga gcaacgcgcg aaccccgcgc tgctcagccg cggcgccagc    480
ggcacgcccg gcggccgcag cgtcagggat gacggctact gctcagctag cagcacgccc    540
agagccttcg acaacaaatc tacgaaaggt tcagtggtga ccctgtcctg ttataagaag    600
gaacccaaaa tacaaataga ggaggaatgc ttctatagtg aaccgaataa acgactcagg    660
acgaatagta tcaagactga ggctgatgat gggcgggaga cgtggggcac gggcgcggac    720
tttctgctct ccatcattgg atttgcagtg gatctcgcca atgtctggcg gttcccgtat    780
ctctgctaca ggaatggcgg tggtgcattc ctgatccctt acacgttgat gctggtgttc    840
ggtgctgttc cactattcta catggagctt atcctcggac agtacaaccg gcagggaccg    900
atcacgctct ggaagatatg cccgctcttc aaaggtgtgg ggttctgcgc ggtgatggtg    960
gctttctacg tctccttcta ctataacgtc atcatcggat gggcgttcta cttcctagtg   1020
tcatcagctc ggtcggagct cccgtgggtg cactgcgaca actcgtggaa cacagaccag   1080
tgctgggcct ccggctggga caacgctacc aacaggactg atgtccgcta ccagggaccg   1140
ctgtcgcact tcacgccggc ttccgagttc tttcatcgag ctgtccttga gatgcagaac   1200
tccgagggtc tgaatgactt gggcttcccg aaatggcaac tggcgatttg cttggggctg   1260
gtgtacgtca ctctctacct gtcgctgttc aaaggcgtca agagctccgg aaaagtggta   1320
tggatgacag caacgatgcc atacgtggtg ctctccatcc tccttgctcg aggactgctg   1380
ctgcccggcg ccacgcgagg catcgcctac tatctgcagc cagaactcac caggctgaag   1440
gatacacaag tgtgggtgga tcggcagtt caaatcttct actctgtcgg cgctggtttt   1500
ggagtccacc tctcgtacgc cagttacaac acgtttcaca ataactgcta cagagactgt   1560
ttggttacga cgctggtcaa ctgtttcacg tcatttttct ccggattcgt aatcttcaca   1620
tatcttggat tcatgtctca taaacaaggc gtaccgatat cgtcagtggc caccgaaggt   1680
cctgggctgg tgttccaagt gtatcccgag gccgtggcga ccctaccggg tgccagtctg   1740
tgggcgatgc tcttcttctt catgctcatc atgctaggat tggattcggg gatgggcggt   1800
ctggagtgcg tgatcaccgg cttgctggac caggcgcgtg cgtgtggtgc cacctggctg   1860
cggcgagaac atttcacccct catcgtcgtc tgtgtatcat tctgcgtggc ctgtattaat   1920
gttacaccgg gcggtatcta catgttccat ctcctagaca cgtatgctgc tggtatctcg   1980
ttgctctgct ccgcgctgtt cgaagccgtt gctgtgtctt ggttctatgg tttgaaacgg   2040
tttttctgatg acgtggagga gatgctcggc ttccgacctg gtctgtactg gaggatatgc   2100
tggaagttcg tcagtcccac cttcattatt ggtgtggtgg tattcgggct gctataccag   2160
cagcctctcc agtaccagca gtacacgtac ccgccgtggg ccgtggtgct gggctggggg   2220
ctggcctgct cctccatcct catgatccca gtcgtcggta tctacaagct catctccacg   2280
```

```
ccggggacat tccgtgagcg cgtggcttgc tgtatttcac cggaatctga gcacgaggcc    2340
attcggggag gcgcccctgt cagccggttc tcctggcgac actggctgta cgtgtaaacg    2400
aacctttatg gctattctgg aagattcgaa taaagaaggt ctatatctta gtcagaaata    2460
ggcgcttcgg agaggaaaaa gagggggaaa aaaaaaaaa aaaa                      2504
```

<210> SEQ ID NO 2
<211> LENGTH: 664
<212> TYPE: PRT
<213> ORGANISM: Trichoplusia ni

<400> SEQUENCE: 2

```
Met Ala Thr Leu Ser Gly Thr Gly Val Val Thr His Thr Ala Pro Ser
1               5                   10                  15

Tyr Glu Glu Gln Arg Ala Asn Pro Ala Leu Leu Ser Arg Gly Ala Ser
            20                  25                  30

Gly Thr Pro Gly Gly Arg Ser Val Arg Asp Asp Gly Tyr Cys Ser Ala
        35                  40                  45

Ser Ser Thr Pro Arg Ala Phe Asp Asn Lys Ser Thr Lys Gly Lys Val
    50                  55                  60

Val Thr Leu Ser Cys Tyr Lys Lys Glu Pro Lys Ile Gln Ile Glu Glu
65                  70                  75                  80

Glu Cys Phe Tyr Ser Glu Pro Asn Lys Arg Leu Arg Thr Asn Ser Ile
                85                  90                  95

Lys Thr Glu Ala Asp Asp Gly Arg Glu Thr Trp Gly Thr Gly Ala Asp
            100                 105                 110

Phe Leu Leu Ser Ile Ile Gly Phe Ala Val Asp Leu Ala Asn Val Trp
        115                 120                 125

Arg Phe Pro Tyr Leu Cys Tyr Arg Asn Gly Gly Ala Phe Leu Ile
    130                 135                 140

Pro Tyr Thr Leu Met Leu Val Phe Gly Ala Val Pro Leu Phe Tyr Met
145                 150                 155                 160

Glu Leu Ile Leu Gly Gln Tyr Asn Arg Gln Gly Pro Ile Thr Leu Trp
                165                 170                 175

Lys Ile Cys Pro Leu Phe Lys Gly Val Gly Phe Cys Ala Val Met Val
            180                 185                 190

Phe Tyr Val Ser Phe Tyr Tyr Asn Val Ile Ile Gly Trp Ala Phe Tyr
        195                 200                 205

Phe Leu Val Ser Ser Ala Arg Ser Glu Leu Pro Trp Val His Cys Asp
    210                 215                 220

Asn Ser Trp Asn Thr Asp Gln Cys Trp Ala Ser Gly Trp Asp Asn Ala
225                 230                 235                 240

Thr Asn Arg Thr Asp Val Arg Tyr Gln Gly Pro Leu Ser His Phe Thr
                245                 250                 255

Pro Ala Ser Glu Phe Phe His Arg Ala Val Leu Glu Met Gln Asn Ser
            260                 265                 270

Glu Gly Leu Asn Asp Leu Gly Phe Pro Lys Trp Gln Leu Ala Ile Cys
        275                 280                 285

Leu Gly Leu Val Tyr Val Thr Leu Tyr Leu Ser Leu Phe Lys Gly Val
    290                 295                 300

Lys Ser Ser Gly Lys Val Val Trp Met Thr Ala Thr Met Pro Tyr Val
305                 310                 315                 320

Val Leu Ser Ile Leu Leu Ala Arg Gly Leu Leu Leu Pro Gly Ala Thr
                325                 330                 335
```

-continued

```
Arg Gly Ile Ala Tyr Tyr Leu Gln Pro Glu Leu Thr Arg Leu Lys Asp
            340                 345                 350

Thr Gln Val Trp Val Asp Ala Val Gln Ile Phe Tyr Ser Val Gly
        355                 360                 365

Ala Gly Phe Gly Val His Leu Ser Tyr Ala Ser Tyr Asn Thr Phe His
        370                 375                 380

Asn Asn Cys Tyr Arg Asp Cys Leu Val Thr Thr Leu Val Asn Cys Phe
385                 390                 395                 400

Thr Ser Phe Phe Ser Gly Phe Val Ile Phe Thr Tyr Leu Gly Phe Met
                405                 410                 415

Ser His Lys Gln Gly Val Pro Ile Ser Ser Val Thr Glu Gly Pro Gly
            420                 425                 430

Leu Val Phe Gln Val Tyr Pro Glu Ala Val Thr Leu Pro Gly Ala Ser
            435                 440                 445

Leu Trp Ala Met Leu Phe Phe Met Leu Ile Met Leu Gly Leu Asp
        450                 455                 460

Ser Gly Met Gly Gly Leu Glu Cys Val Ile Thr Gly Leu Leu Asp Gln
465                 470                 475                 480

Ala Arg Ala Cys Gly Ala Thr Trp Leu Arg Arg Glu His Phe Thr Leu
                485                 490                 495

Ile Val Val Cys Val Ser Phe Cys Val Cys Ile Asn Val Thr Pro Gly
                500                 505                 510

Gly Ile Tyr Met Phe His Leu Leu Asp Thr Tyr Ala Ala Gly Ile Ser
        515                 520                 525

Leu Leu Cys Ser Ala Leu Phe Glu Ala Val Val Ser Trp Phe Tyr Gly
        530                 535                 540

Leu Lys Arg Phe Ser Asp Asp Val Glu Glu Met Leu Gly Phe Arg Pro
545                 550                 555                 560

Gly Leu Tyr Trp Arg Ile Cys Trp Lys Phe Val Ser Pro Thr Phe Ile
                565                 570                 575

Ile Gly Val Val Val Phe Gly Leu Leu Tyr Gln Gln Pro Leu Gln Tyr
                580                 585                 590

Gln Gln Tyr Thr Tyr Pro Pro Trp Ala Val Val Leu Gly Trp Gly Leu
            595                 600                 605

Ala Cys Ser Ser Ile Leu Met Ile Pro Val Val Gly Ile Tyr Lys Leu
        610                 615                 620

Ile Ser Thr Pro Gly Thr Phe Arg Glu Arg Val Cys Cys Ile Ser Pro
625                 630                 635                 640

Glu Ser Glu His Glu Ala Ile Arg Gly Gly Ala Pro Val Ser Arg Phe
                645                 650                 655

Ser Trp Arg His Trp Leu Tyr Val
            660

<210> SEQ ID NO 3
<211> LENGTH: 8
<212> TYPE: PRT
<213> ORGANISM: Artificial Sequence
<220> FEATURE:
<223> OTHER INFORMATION: Conserved DAT1 peptide sequence

<400> SEQUENCE: 3

Gly Met Pro Leu Phe Tyr Met Glu
 1               5

<210> SEQ ID NO 4
<211> LENGTH: 8
```

<212> TYPE: PRT
<213> ORGANISM: Artificial Sequence
<220> FEATURE:
<223> OTHER INFORMATION: Conserved DAT2 peptide sequence

<400> SEQUENCE: 4

Trp Lys Gly Val Lys Thr Ser Gly
 1               5

<210> SEQ ID NO 5
<211> LENGTH: 8
<212> TYPE: PRT
<213> ORGANISM: Artificial Sequence
<220> FEATURE:
<223> OTHER INFORMATION: Conserved DAT3 peptide sequence

<400> SEQUENCE: 5

Lys Val Val Trp Ile Thr Ala Thr
 1               5

<210> SEQ ID NO 6
<211> LENGTH: 7
<212> TYPE: PRT
<213> ORGANISM: Artificial Sequence
<220> FEATURE:
<223> OTHER INFORMATION: Conserved GABA1 transporter peptide sequence

<400> SEQUENCE: 6

Asn Val Trp Arg Phe Pro Tyr
 1               5

<210> SEQ ID NO 7
<211> LENGTH: 9
<212> TYPE: PRT
<213> ORGANISM: Artificial Sequence
<220> FEATURE:
<223> OTHER INFORMATION: Conserved GABA2 transporter peptide sequence

<400> SEQUENCE: 7

Ser Lys Trp Gly Lys Trp Ile Cys Phe
 1               5

<210> SEQ ID NO 8
<211> LENGTH: 24
<212> TYPE: DNA
<213> ORGANISM: Artificial Sequence
<220> FEATURE:
<223> OTHER INFORMATION: PCR primer BKRev

<400> SEQUENCE: 8
acaggaaaca gctatgacct tgat                                          24

<210> SEQ ID NO 9
<211> LENGTH: 24
<212> TYPE: DNA
<213> ORGANISM: Artificial Sequence
<220> FEATURE:
<223> OTHER INFORMATION: PCR primer T3+

<400> SEQUENCE: 9
cctcactaaa gggaacaaaa gctg                                          24

<210> SEQ ID NO 10
<211> LENGTH: 24
<212> TYPE: DNA
<213> ORGANISM: Artificial Sequence
<220> FEATURE:

-continued

<223> OTHER INFORMATION: PCR primer BKFor

<400> SEQUENCE: 10
gtaaaacgac ggccagtgaa ttgt                                    24

<210> SEQ ID NO 11
<211> LENGTH: 24
<212> TYPE: DNA
<213> ORGANISM: Artificial Sequence
<220> FEATURE:
<223> OTHER INFORMATION: PCR primer T7+

<400> SEQUENCE: 11
acgactcact atagggcgaa ttgg                                    24

<210> SEQ ID NO 12
<211> LENGTH: 22
<212> TYPE: DNA
<213> ORGANISM: Artificial Sequence
<220> FEATURE:
<223> OTHER INFORMATION: PCR primer For1

<400> SEQUENCE: 12
accactttcc ggagctcttg ac                                      22

<210> SEQ ID NO 13
<211> LENGTH: 24
<212> TYPE: DNA
<213> ORGANISM: Artificial Sequence
<220> FEATURE:
<223> OTHER INFORMATION: PCR primer For2

<400> SEQUENCE: 13
ctttgaacag cgacaggtag agag                                    24

<210> SEQ ID NO 14
<211> LENGTH: 24
<212> TYPE: DNA
<213> ORGANISM: Artificial Sequence
<220> FEATURE:
<223> OTHER INFORMATION: PCR primer Rev1

<400> SEQUENCE: 14
acatggagct tatcttcgga cagt                                    24

<210> SEQ ID NO 15
<211> LENGTH: 23
<212> TYPE: DNA
<213> ORGANISM: Artificial Sequence
<220> FEATURE:
<223> OTHER INFORMATION: PCR primer Rev2

<400> SEQUENCE: 15
agggaccgat cacgctctgg aag                                     23

<210> SEQ ID NO 16
<211> LENGTH: 24
<212> TYPE: DNA
<213> ORGANISM: Artificial Sequence
<220> FEATURE:
<223> OTHER INFORMATION: Downstream primer

<400> SEQUENCE: 16
cttgtttcta cataaattta ttcc                                    24

<210> SEQ ID NO 17
<211> LENGTH: 25
<212> TYPE: DNA
<213> ORGANISM: Artificial Sequence
<220> FEATURE:
<223> OTHER INFORMATION: Upstream primer

<400> SEQUENCE: 17
aacaacattt atctctacac tgcta                                            25

<210> SEQ ID NO 18
<211> LENGTH: 24
<212> TYPE: DNA
<213> ORGANISM: Artificial Sequence
<220> FEATURE:
<223> OTHER INFORMATION: Upstream primer

<400> SEQUENCE: 18
ggccaaggtc atccatgaca actt                                             24

<210> SEQ ID NO 19
<211> LENGTH: 27
<212> TYPE: DNA
<213> ORGANISM: Artificial Sequence
<220> FEATURE:
<223> OTHER INFORMATION: 5'UTR-BamHI PCR primer

<400> SEQUENCE: 19
gcggatccac gcacaggacc atgagac                                          27

<210> SEQ ID NO 20
<211> LENGTH: 27
<212> TYPE: DNA
<213> ORGANISM: Artificial Sequence
<220> FEATURE:
<223> OTHER INFORMATION: 3'UTR-KpnI PCR primer

<400> SEQUENCE: 20
cgggtaccga agcgcctatt tctgact                                          27

<210> SEQ ID NO 21
<211> LENGTH: 444
<212> TYPE: DNA
<213> ORGANISM: Artificial Sequence
<220> FEATURE:
<223> OTHER INFORMATION: Consensus nucleotide sequence for SEQ ID
      NOS:22-30

<400> SEQUENCE: 21
ctgatcctgg gccagtacaa ccggcaagga cccatcactc tatgaagat ttgcccactg        60 ttcaaaggtg ttggattctg cgcggtcatg gtggctttct acgtttcgtt ctactacaac      120
gttattattg gctgggcttt ctacttcctg gtgtcgtcag ctcgctcgga gctgccgtgg      180
gtgcactgcg acaactcctg gaacacggag cagtgctggg acgccgcacg gctcaacgcc      240
accaacagga ctgatgtacc gtaccaggga cctctgtcgc acttcacacc agcttctgag      300
ttctttcatc gtgctgtcct tgaaatgcag cattcggaag gtctgaatga cttgggcttc      360
ccgaaatggc aactggctat tgcttgggg ctggtctacg tcacgctcta cctttcactg      420
ttcaaaggag tcaagagttc tggt                                            444

<210> SEQ ID NO 22
<211> LENGTH: 444
<212> TYPE: DNA
<213> ORGANISM: Trichoplusia ni

<400> SEQUENCE: 22

```
cttatcctcg gacagtacaa ccggcaggga ccgatcacgc tctggaagat atgcccgctc      60
ttcaaaggtg tggggttctg cgcggtgatg gtggctttct acgtctcctt ctactataac     120
gtcatcatcg gatgggcgtt ctacttccta gtgtcatcag ctcggtcgga gctcccgtgg     180
gtgcactgcg acaactcgtg gaacacagac cagtgctggg actccggccg ggacaacgct     240
accaacagga ctgatgtccg ctaccaggga ccgctgtcgc acttcacgcc ggcttccgag     300
ttctttcatc gagctgtcct tgagatgcag aactccgagg gtctgaatga cttgggcttc     360
ccgaaatggc aactggcgat tgcttgggg ctggtgtacg tcactctcta cctgtcgctg      420
ttcaaaggcg tcaagagctc cgga                                           444
```

<210> SEQ ID NO 23
<211> LENGTH: 450
<212> TYPE: DNA
<213> ORGANISM: Agriotis epsilon

<400> SEQUENCE: 23

```
ctgatcctcg gccagtacaa ccgacaggga cccatcacct tgtggaakat ttgcccacty      60
ttcaaaggtg tsggattctg tgcggtcatg gtggctttct acgtgtcgtt ttactacaac     120
gtcatcattg gctgggcgtt gtacttcctc atatcgtcag cgcgctcrga gctgccctgg     180
gtgcactgcg acaactcgtg gaacacggag cagtgctggg actccggagg cgcagtcaac     240
gccaccagca atagaactga cgtgcggtat caaggaccct tgtcgcactt cactccagct     300
tcagagttct tccaccgtgc agttttggaa atgcaacact ctgaaggtct gaacgatctc     360
ggcttcccga atggcaact ggcaatctgc ttgggactgg tctacgtcac gctgtattta      420
tcactsttca arggmgtcaa gagctctggt                                      450
```

<210> SEQ ID NO 24
<211> LENGTH: 444
<212> TYPE: DNA
<213> ORGANISM: Bombyx mori

<400> SEQUENCE: 24

```
ttgatcctmg ggcagtataa ccgacaagga cctatcactc tatggaaaat atgtccattg      60
tttaaaggtg ttggattctg cgcagtcatg gttgcgtttt atgtttcctt ctattataat     120
gtaataattg gctgggcttt ctacttcttg atgtcgtcag ctcgatcaga actgccatgg     180
gtgcattgcg ataattcttg gaacacggaa caatgttggg actcggctcg gttgaatggt     240
accaatcgca cggatgttaa ataccaagga ccactgtcgc atttcacgcc tgcttcagaa     300
ttctttcatc gagcagtcct ggaaatgcag cattcggaag gtttgaatga tctaggtttg     360
ccgaaatggc aattggctgc ttgtctcggt tggtctatg taactttata cctttcatta      420
ttcaaaggcg ttaagagctc cgga                                           444
```

<210> SEQ ID NO 25
<211> LENGTH: 444
<212> TYPE: DNA
<213> ORGANISM: Calpodes ethlius

<400> SEQUENCE: 25

```
ttaatactgg gccagtacaa ccgtcaagga ccyatwacgt tgtggaagat ctgtccgttg      60
ttcaaaggtg tcggtttctg cgctgtaatg gtcgccttt acgtgtcatt ttattataac     120
```

```
gtgattattg gctgggcttt ctacttcctg gtgtcgtcag cccgttcgga gctgccctgg    180
gtgcactgtg acaacgcctg gaataccgag cagtgctggg acgctgccag gctcaacgct    240
accaacagaa ctgatgtacc ctaccagggt cctctgtctc acttcacacc agcctccgag    300
ttctttcatc gcgctgttct tgaaatgcag cattctgaag gtctcaatga cctgggacta    360
ccgaaatggc agttggctct tgcttaggg gttgtctaca tcaccctcta tctctcactg    420
ttcaaaggcg ttaaaagttc aggt                                           444
```

<210> SEQ ID NO 26
<211> LENGTH: 444
<212> TYPE: DNA
<213> ORGANISM: Choristoneura fumiferana

<400> SEQUENCE: 26

```
ctgatactgg gccagtacaa caggcaaggc cccatcacta tctggaagat atgccctcta     60
tttaaaggtg ttggattttg tgctgtcatg gtagcattct acgtttcgtt ctactacaac    120
gtgattatcg gctgggcctt ttatttcctg gtgtcatctg cccgctccga gctgccttgg    180
ctgcactgcg acaacgcctg gaacaccgag cagtgctggg acgccgcgcg cacaacgcg    240 accaacaaga ccgaagtacc gtaccagggg ccgctgtcgc acttcacacc agcatctgaa    300
ttcttccacc gagctgtcct tgagatgcaa tattccgaag gctgaacga cttgggcttc    360 ccgaaatggc aactagccct gcctcgct ctggtgtact tcacgctcta cctctcgctc    420
ttcaaaggag taaagagttc tggt                                           444
```

<210> SEQ ID NO 27
<211> LENGTH: 444
<212> TYPE: DNA
<213> ORGANISM: Ostrinia nubilalis

<400> SEQUENCE: 27

```
ctcattctgg gacagtacaa ccgacaaggg cccataacta tatggaagat ctgcccattg     60
ttcaaaggtg ttggattttg tgcggtgatg gtcgcatttt acgtatcatt ttactataat    120
gttattattg gttgggcttt ctactttctg gtatcgtcag ctcgctcaga gctcccgtgg    180
gtgcactgcg acaacgcctg gaacaccgac cagtgctggg atgccgcaag gctcaacaac    240
accaaccgga ccgaaatacc ttatcaagga cctttgtcgc acttcacacc ggcttcggag    300
ttctttcacc gggcagtgct cgagatgcaa cactcggaag gcctcaatga cttgggcttc    360
cccaaatggc agctcacagt ttgcctcggg ctcgtctacg tcacgttata cctttctctc    420
tttaaaggag tcaaaagttc tgga                                           444
```

<210> SEQ ID NO 28
<211> LENGTH: 444
<212> TYPE: DNA
<213> ORGANISM: Lambdina fiscallari

<400> SEQUENCE: 28

```
ctgatcctgg gccagtacaa ccggcaaggg cccatcacac tttggaagat ctgcccsctc     60
ttcaaagggg tgggkttctg cgccgtgatg gtggcgttct acgtctcgtt ctactacaac    120
gttatcattg gctgggcatt ctacttcctg gtgtcgtcgg cgcggtcgga gctgccgtgg    180
ctgcactgcg acaactcctg gaacacggag cagtgctggg acgccacgag agccaatgtc    240
accaacaaga cggaactcrc gtatcagggc ccgctctcgc acttcacgcc agcttccgag    300
ttctttcatc gtgcagtcct sgaaatgcag tactcagagg gactcaacga cctcggcttt    360
```

```
ccaaaatggc agctagctat gtgcttgggc ttggtctacg tcactctcta tctgtcactg      420
ttcaarggag tcaaaagttc tggc                                              444

<210> SEQ ID NO 29
<211> LENGTH: 444
<212> TYPE: DNA
<213> ORGANISM: Pieris rapae

<400> SEQUENCE: 29
ctgattttgg gccaatacaa tcgacagggc cctataactc tatggaaaat ttgtccactt       60 ttcaaggtg tgggattttg ygcagttatg gtggcgtttt acgtttcttt ctattacaac       120
gttattatcg ggtgggcact ctacttcctc gtatcatcag ctcgttcaga acttccctgg     180
ctacattgta acaacctgtg gaatactgat caatgytggg atgcctcaag acaaaacaca     240
accaacaaga cggacatttc ataccagggc cctttgtcac atttcacacc agcatctgag     300
ttctttcatc gtgcggtact tgaaatgcaa tattcggaag gattgaatga cttgggtttc     360
ccaaaatggc agctcactat ttgcttrgga atcgtttaca taacgttgta cctatcgctg     420
ttcaaaggag tcaaragttc cggt                                              444

<210> SEQ ID NO 30
<211> LENGTH: 445
<212> TYPE: DNA
<213> ORGANISM: Manduca cinquemaculata

<400> SEQUENCE: 30
dctgattttg ggtcagtaca accggcaagg acctatcacg ctatggaaga tttgccccctt      60 attcaaaggt gttggattct cgcagtcat ggtggctttc tacgtatctt tttactacaa       120
tgtcatcata ggatgggcgt tctacttcct aatatcatca gcccgctccg agctcccgtg     180
ggtgcactgc gacaactcct ggaatacgga gcagtgttgg gacgcggctc ggctgaacgc     240
caccaaccgg accgatgtga agtaccaggg acccttgtcg cattttaccc cggcttctga     300
gttctttcac cgtgctgtcc tcgaaatgca gcattcagaa ggacttaacg acttgggctt     360
tccgaaatgg caactggctg tctgtttggg attggtttac gtgacgcttt acctttctct     420
cttcaaagga gtcaagagtt cgggc                                            445

<210> SEQ ID NO 31
<211> LENGTH: 592
<212> TYPE: PRT
<213> ORGANISM: Artificial Sequence
<220> FEATURE:
<223> OTHER INFORMATION: Consensus sequence of SEQ ID NOS:32-40

<400> SEQUENCE: 31

Cys Thr Gly Ala Thr Thr Thr Gly Gly Gly Thr Cys Ala Gly Thr
1               5                   10                  15

Ala Cys Ala Ala Cys Cys Gly Gly Cys Ala Ala Gly Gly Ala Cys Cys
                20                  25                  30

Thr Ala Thr Cys Ala Cys Gly Cys Thr Ala Thr Gly Gly Ala Ala Gly
                35                  40                  45

Ala Thr Thr Thr Gly Cys Cys Cys Thr Thr Ala Thr Thr Cys Ala
        50                  55                  60

Ala Ala Gly Gly Thr Gly Thr Thr Gly Gly Ala Thr Thr Cys Thr Gly
65                  70                  75                  80

Cys Gly Cys Ala Gly Thr Cys Ala Thr Gly Gly Thr Gly Gly Cys Thr
```

-continued

```
                    85                  90                  95
Thr Thr Cys Thr Ala Cys Gly Thr Ala Cys Thr Thr Thr Thr
            100                 105                 110
Ala Cys Thr Ala Cys Ala Ala Thr Gly Thr Cys Ala Thr Cys Ala Thr
            115                 120                 125
Ala Gly Gly Ala Thr Gly Gly Cys Gly Thr Thr Cys Thr Ala Cys
130                 135                 140
Thr Thr Cys Cys Thr Ala Ala Thr Ala Thr Cys Ala Thr Cys Ala Gly
145                 150                 155                 160
Cys Cys Cys Gly Cys Thr Cys Cys Gly Ala Gly Cys Thr Cys Cys Cys
                165                 170                 175
Gly Thr Gly Gly Thr Gly Cys Ala Cys Thr Gly Cys Gly Ala Cys
            180                 185                 190
Ala Ala Cys Thr Cys Cys Thr Gly Gly Ala Ala Thr Ala Cys Gly Gly
            195                 200                 205
Ala Gly Cys Ala Gly Thr Gly Thr Thr Gly Gly Gly Ala Cys Gly Cys
            210                 215                 220
Gly Gly Cys Thr Cys Gly Gly Cys Thr Gly Ala Ala Cys Gly Cys Cys
225                 230                 235                 240
Ala Cys Cys Ala Ala Cys Cys Gly Gly Ala Cys Cys Gly Ala Thr Gly
                245                 250                 255
Thr Gly Ala Ala Gly Thr Ala Cys Cys Ala Gly Gly Ala Cys Cys
            260                 265                 270
Cys Thr Thr Gly Thr Cys Gly Cys Ala Thr Thr Thr Ala Cys Cys
        275                 280                 285
Cys Cys Gly Gly Cys Thr Thr Cys Thr Gly Ala Gly Thr Thr Cys Thr
        290                 295                 300
Thr Thr Cys Ala Cys Cys Gly Thr Gly Cys Thr Gly Thr Cys Cys Thr
305                 310                 315                 320
Cys Gly Ala Ala Ala Thr Gly Cys Ala Gly Cys Ala Thr Thr Cys Ala
                325                 330                 335
Gly Ala Ala Gly Gly Ala Cys Thr Thr Ala Ala Cys Gly Ala Cys Thr
            340                 345                 350
Thr Gly Gly Gly Cys Thr Thr Thr Cys Cys Gly Ala Ala Ala Thr Gly
            355                 360                 365
Gly Cys Ala Ala Cys Thr Gly Gly Cys Thr Gly Thr Cys Thr Gly Thr
        370                 375                 380
Thr Thr Gly Gly Gly Ala Thr Gly Gly Thr Thr Ala Cys Gly
385                 390                 395                 400
Thr Gly Ala Cys Gly Cys Thr Thr Ala Cys Cys Thr Thr Thr Cys
                405                 410                 415
Thr Cys Thr Cys Thr Thr Cys Ala Ala Ala Gly Gly Ala Gly Thr Cys
            420                 425                 430
Ala Ala Gly Ala Gly Thr Thr Cys Gly Gly Gly Cys Leu Ile Leu Gly
        435                 440                 445
Gln Tyr Asn Arg Gln Gly Pro Ile Thr Leu Trp Lys Ile Cys Pro Leu
450                 455                 460
Phe Lys Gly Val Gly Phe Cys Ala Val Met Val Ala Phe Tyr Val Ser
465                 470                 475                 480
Phe Tyr Tyr Asn Val Ile Ile Gly Trp Ala Phe Tyr Phe Leu Val Ser
                485                 490                 495
Ser Ala Arg Ser Glu Leu Pro Trp Val His Cys Asp Asn Ser Trp Asn
            500                 505                 510
```

Thr Glu Gln Cys Trp Asp Ala Ala Arg Leu Asn Ala Thr Asn Arg Thr
            515                 520                 525

Asp Val Pro Tyr Gln Gly Pro Leu Ser His Phe Thr Pro Ala Ser Glu
        530                 535                 540

Phe Phe His Arg Ala Val Leu Glu Met Gln His Ser Glu Gly Leu Asn
545                 550                 555                 560

Asp Leu Gly Phe Pro Lys Trp Gln Leu Ala Ile Cys Leu Gly Leu Val
                565                 570                 575

Tyr Val Thr Leu Tyr Leu Ser Leu Phe Lys Gly Val Lys Ser Ser Gly
                580                 585                 590

<210> SEQ ID NO 32
<211> LENGTH: 148
<212> TYPE: PRT
<213> ORGANISM: Trichoplusia ni

<400> SEQUENCE: 32

Leu Ile Leu Gly Gln Tyr Asn Arg Gln Gly Pro Ile Thr Leu Trp Lys
1               5                   10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Phe Tyr
        35                  40                  45

Phe Leu Val Ser Ser Ala Arg Ser Glu Leu Pro Trp Val His Cys Asp
    50                  55                  60

Asn Ser Trp Asn Thr Asp Gln Cys Trp Asp Ser Gly Arg Asp Asn Ala
65                  70                  75                  80

Thr Asn Arg Thr Asp Val Arg Tyr Gln Gly Pro Leu Ser His Phe Thr
                85                  90                  95

Pro Ala Ser Glu Phe Phe His Arg Ala Val Leu Glu Met Gln Asn Ser
            100                 105                 110

Glu Gly Leu Asn Asp Leu Gly Phe Pro Lys Trp Gln Leu Ala Ile Cys
        115                 120                 125

Leu Gly Leu Val Tyr Val Thr Leu Tyr Leu Ser Leu Phe Lys Gly Val
    130                 135                 140

Lys Ser Ser Gly
145

<210> SEQ ID NO 33
<211> LENGTH: 150
<212> TYPE: PRT
<213> ORGANISM: Agriotis epsilon

<400> SEQUENCE: 33

Leu Ile Leu Gly Gln Tyr Asn Arg Gln Gly Pro Ile Thr Leu Trp Lys
1               5                   10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Leu Tyr
        35                  40                  45

Phe Leu Ile Ser Ser Ala Arg Ser Glu Leu Pro Trp Val His Cys Asp
    50                  55                  60

Asn Ser Trp Asn Thr Glu Gln Cys Trp Asp Ser Gly Gly Ala Val Asn
65                  70                  75                  80

Ala Thr Ser Asn Arg Thr Asp Val Arg Tyr Gln Gly Pro Leu Ser His
                85                  90                  95

```
Phe Thr Pro Ala Ser Glu Phe Phe His Arg Ala Val Leu Glu Met Gln
                100                 105                 110

His Ser Glu Gly Leu Asn Asp Leu Gly Phe Pro Lys Trp Gln Leu Ala
            115                 120                 125

Ile Cys Leu Gly Leu Val Tyr Val Thr Leu Tyr Leu Ser Leu Phe Lys
        130                 135                 140

Gly Val Lys Ser Ser Gly
145                 150

<210> SEQ ID NO 34
<211> LENGTH: 148
<212> TYPE: PRT
<213> ORGANISM: Bombyx mori

<400> SEQUENCE: 34

Leu Ile Leu Gly Gln Tyr Asn Arg Gln Gly Pro Ile Thr Leu Trp Lys
1               5                   10                  15

Ile Cys Pro Leu Phe Lys Gly Val Gly Phe Cys Ala Val Met Val Ala
                20                  25                  30

Phe Tyr Val Ser Phe Tyr Tyr Asn Val Ile Ile Gly Trp Ala Phe Tyr
            35                  40                  45

Phe Leu Met Ser Ser Ala Arg Ser Glu Leu Pro Trp Val His Cys Asp
        50                  55                  60

Asn Ser Trp Asn Thr Glu Gln Cys Trp Asp Ser Ala Arg Leu Asn Gly
65                  70                  75                  80

Thr Asn Arg Thr Asp Val Lys Tyr Gln Gly Pro Leu Ser His Phe Thr
                85                  90                  95

Pro Ala Ser Glu Phe Phe His Arg Ala Val Leu Glu Met Gln His Ser
            100                 105                 110

Glu Gly Leu Asn Asp Leu Gly Leu Pro Lys Trp Gln Leu Ala Ala Cys
        115                 120                 125

Leu Gly Leu Val Tyr Val Thr Leu Tyr Leu Ser Leu Phe Lys Gly Val
    130                 135                 140

Lys Ser Ser Gly
145

<210> SEQ ID NO 35
<211> LENGTH: 148
<212> TYPE: PRT
<213> ORGANISM: Calpodes ethlius

<400> SEQUENCE: 35

Leu Ile Leu Gly Gln Tyr Asn Arg Gln Gly Pro Ile Thr Leu Trp Lys
1               5                   10                  15

Ile Cys Pro Leu Phe Lys Gly Val Gly Phe Cys Ala Val Met Val Ala
                20                  25                  30

Phe Tyr Val Ser Phe Tyr Tyr Asn Val Ile Ile Gly Trp Ala Phe Tyr
            35                  40                  45

Phe Leu Val Ser Ser Ala Arg Ser Glu Leu Pro Trp Val His Cys Asp
        50                  55                  60

Asn Ala Trp Asn Thr Glu Gln Cys Trp Asp Ala Ala Arg Leu Asn Ala
65                  70                  75                  80

Thr Asn Arg Thr Asp Val Pro Tyr Gln Gly Pro Leu Ser His Phe Thr
                85                  90                  95

Pro Ala Ser Glu Phe Phe His Arg Ala Val Leu Glu Met Gln His Ser
            100                 105                 110
```

```
Glu Gly Leu Asn Asp Leu Gly Leu Pro Lys Trp Gln Leu Ala Leu Cys
            115                 120                 125

Leu Gly Val Val Tyr Ile Thr Leu Tyr Leu Ser Leu Phe Lys Gly Val
        130                 135                 140

Lys Ser Ser Gly
145

<210> SEQ ID NO 36
<211> LENGTH: 148
<212> TYPE: PRT
<213> ORGANISM: Choristoneura fumiferana

<400> SEQUENCE: 36

Leu Ile Leu Gly Gln Tyr Asn Arg Gln Gly Pro Ile Thr Ile Trp Lys
1               5                   10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Phe Tyr
        35                  40                  45

Phe Leu Val Ser Ser Ala Arg Ser Glu Leu Pro Trp Leu His Cys Asp
    50                  55                  60

Asn Ala Trp Asn Thr Glu Gln Cys Trp Asp Ala Ala Arg His Asn Ala
65                  70                  75                  80

Thr Asn Lys Thr Glu Val Pro Tyr Gln Gly Pro Leu Ser His Phe Thr
                85                  90                  95

Pro Ala Ser Glu Phe Phe His Arg Ala Val Leu Glu Met Gln Tyr Ser
            100                 105                 110

Glu Gly Leu Asn Asp Leu Gly Phe Pro Lys Trp Gln Leu Ala Leu Cys
            115                 120                 125

Leu Ala Leu Val Tyr Phe Thr Leu Tyr Leu Ser Leu Phe Lys Gly Val
        130                 135                 140

Lys Ser Ser Gly
145

<210> SEQ ID NO 37
<211> LENGTH: 148
<212> TYPE: PRT
<213> ORGANISM: Ostrinia nubilalis

<400> SEQUENCE: 37

Leu Ile Leu Gly Gln Tyr Asn Arg Gln Gly Pro Ile Thr Ile Trp Lys
1               5                   10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Phe Tyr
        35                  40                  45

Phe Leu Val Ser Ser Ala Arg Ser Glu Leu Pro Trp Val His Cys Asp
    50                  55                  60

Asn Ala Trp Asn Thr Asp Gln Cys Trp Asp Ala Ala Arg Leu Asn Asn
65                  70                  75                  80

Thr Asn Arg Thr Glu Ile Pro Tyr Gln Gly Pro Leu Ser His Phe Thr
                85                  90                  95

Pro Ala Ser Glu Phe Phe His Arg Ala Val Leu Glu Met Gln His Ser
            100                 105                 110

Glu Gly Leu Asn Asp Leu Gly Phe Pro Lys Trp Gln Leu Thr Val Cys
            115                 120                 125
```

Leu Gly Leu Val Tyr Val Thr Leu Tyr Leu Ser Leu Phe Lys Gly Val
            130                 135                 140

Lys Ser Ser Gly
145

<210> SEQ ID NO 38
<211> LENGTH: 148
<212> TYPE: PRT
<213> ORGANISM: Lambdina fiscallari
<220> FEATURE:
<221> NAME/KEY: VARIANT
<222> LOCATION: (1)...(148)
<223> OTHER INFORMATION: Xaa = Any Amino Acid

<400> SEQUENCE: 38

Leu Ile Leu Gly Gln Tyr Asn Arg Gln Gly Pro Ile Thr Leu Trp Lys
 1               5                  10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Phe Tyr
            35                  40                  45

Phe Leu Val Ser Ser Ala Arg Ser Glu Leu Pro Trp Leu His Cys Asp
        50                  55                  60

Asn Ser Trp Asn Thr Glu Gln Cys Trp Asp Ala Thr Arg Ala Asn Val
65                  70                  75                  80

Thr Asn Lys Thr Glu Leu Xaa Tyr Gln Gly Pro Leu Ser His Phe Thr
                85                  90                  95

Pro Ala Ser Glu Phe Phe His Arg Ala Val Leu Glu Met Gln Tyr Ser
            100                 105                 110

Glu Gly Leu Asn Asp Leu Gly Phe Pro Lys Trp Gln Leu Ala Met Cys
        115                 120                 125

Leu Gly Leu Val Tyr Val Thr Leu Tyr Leu Ser Leu Phe Lys Gly Val
    130                 135                 140

Lys Ser Ser Gly
145

<210> SEQ ID NO 39
<211> LENGTH: 148
<212> TYPE: PRT
<213> ORGANISM: Pieris rapae

<400> SEQUENCE: 39

Leu Ile Leu Gly Gln Tyr Asn Arg Gln Gly Pro Ile Thr Leu Trp Lys
 1               5                  10                  15

Ile Cys Pro Leu Phe Lys Gly Val Gly Phe Cys Ala Val Met Val Ala
            20                  25                  30

Phe Tyr Val Ser Phe Tyr Tyr Asn Val Ile Ile Gly Trp Ala Leu Tyr
            35                  40                  45

Phe Leu Val Ser Ser Ala Arg Ser Glu Leu Pro Trp Leu His Cys Asn
        50                  55                  60

Asn Leu Trp Asn Thr Asp Gln Cys Trp Asp Ala Ser Arg Gln Asn Thr
65                  70                  75                  80

Thr Asn Lys Thr Asp Ile Ser Tyr Gln Gly Pro Leu Ser His Phe Thr
                85                  90                  95

Pro Ala Ser Glu Phe Phe His Arg Ala Val Leu Glu Met Gln Tyr Ser
            100                 105                 110

Glu Gly Leu Asn Asp Leu Gly Phe Pro Lys Trp Gln Leu Thr Ile Cys

-continued

```
              115                 120                 125
Leu Gly Ile Val Tyr Ile Thr Leu Tyr Leu Ser Leu Phe Lys Gly Val
        130                 135                 140

Lys Ser Ser Gly
145

<210> SEQ ID NO 40
<211> LENGTH: 148
<212> TYPE: PRT
<213> ORGANISM: Manduca cinquemaculata

<400> SEQUENCE: 40

Leu Ile Leu Gly Gln Tyr Asn Arg Gln Gly Pro Ile Thr Leu Trp Lys
 1               5                  10                  15

Ile Cys Pro Leu Phe Lys Gly Val Gly Phe Cys Ala Val Met Val Ala
             20                  25                  30

Phe Tyr Val Ser Phe Tyr Tyr Asn Val Ile Ile Gly Trp Ala Phe Tyr
             35                  40                  45

Phe Leu Ile Ser Ser Ala Arg Ser Glu Leu Pro Trp Val His Cys Asp
         50                  55                  60

Asn Ser Trp Asn Thr Glu Gln Cys Trp Asp Ala Ala Arg Leu Asn Ala
65                  70                  75                  80

Thr Asn Arg Thr Asp Val Lys Tyr Gln Gly Pro Leu Ser His Phe Thr
                 85                  90                  95

Pro Ala Ser Glu Phe Phe His Arg Ala Val Leu Glu Met Gln His Ser
             100                 105                 110

Glu Gly Leu Asn Asp Leu Gly Phe Pro Lys Trp Gln Leu Ala Val Cys
         115                 120                 125

Leu Gly Leu Val Tyr Val Thr Leu Tyr Leu Ser Leu Phe Lys Gly Val
         130                 135                 140

Lys Ser Ser Gly
145
```

INSECT MONOAMINE TRANSPORTER AND METHODS OF USE THEREOF

CROSS-REFERENCE TO RELATED APPLICATION

This application is a continuation-in-part of U.S. patent application Ser. No. 09/587,811, filed on Jun. 6, 2000, issued on Jan. 13, 2004 as U.S. Pat. No. 6,677,443, which claims the benefit of U.S. Application Ser. No. 60/137,929, filed on Jun. 7, 1999, both of which are incorporated herein by reference in their entireties.

BACKGROUND OF INVENTION

Neurotransmitter transporters can be classified into three different families based on their amino acid sequence similarities and the type of gradient used for transport. The first family, the $Na^+/Cl^-$ dependent neurotransmitter transporter family, contains integral membrane glycoproteins that have twelve putative transmembrane domains and use sodium and chloride gradients to transport neurotransmitters across the plasma membrane. The members of this family can be subdivided into four subfamilies based on the type of neurotransmitter transported and specific molecular features of the proteins: (1) monoamine transporters, (2) GABA, betaine, taurine and creatine transporters, (3) glycine and L-proline transporters and (4) orphan clones. The second family, the $Na^+/K^+$ dependent glutamate transporter family, contains plasma membrane glycoproteins that have six to nine putative transmembrane domains, require $K^+$ ions and use $Na^+$ gradients as a driving force to transport the neurotransmitters across plasma membrane. The third family, the proton dependent vesicular transporter family, contains proteins powered by proton gradients to pump the neurotransmitter from the cytosol into synaptic vesicles.

The members of the monoamine subfamily of $Na^+/Cl^-$ dependent neurotransmitter transporters include transporters for: dopamine (DA), norepinephrine (NE), serotonin (SER) and L-epinephrine (E). Most of the cloned monoamine transporters have been isolated from mammals. Monoamine transporters have also been isolated from fruit fly and frog. The cDNA sequences of these transporters made available by molecular cloning reveal features common to all monoamine transporters. The deduced amino acid sequences of all cloned monoamine transporters indicate the presence of twelve putative transmembrane domains, two highly conserved cysteine residues on the large second extracellular loop, conserved consensus sequences for two to four N-linked glycosylation sites and phosphorylation sites on the intracellular domains for protein kinase C (PKC), cAMP-dependent protein kinase (PKA) and $Ca^{2+}$/calmodulin-dependent protein kinase (reviewed by Kitayama and Dohi, (1996) *Jpn J. Pharmacol.* 72: 195).

Insect neurotransmission, like that in mammals, is mediated by several types of neurotransmitters: biogenic amines, amino acids, neuropeptides and nitric oxide. Among the monoamines known to participate in insect neurotransmission are: octopamine (OA), dopamine (DA), serotonin (SER), histamine and possibly tyramine (TA) (Osborne (1996) *Pharmacol. Ther.* 69: 117).

OA, first discovered in the salivary glands of octopus, has been shown to be present in high concentrations in several insect nervous tissues. OA is a phenolamine, the monohydroxylic analogue of norepinephrine (NE). Based on OA's similarity in structure to NE and the fact that OA appears to play many of the roles that NE plays in mammalian systems, it has been called "the insect norepinephrine". Several studies have shown that in insects, OA functions as neurohormone, neuromodulator and neurotransmitter (reviewed by Evans (1985) Octopamine. *Comprehensive Insect Physiology, Biochemistry and Pharmacology*. Volume 2, Kerkut et al., eds., Pergamon Place, Oxford).

In the insect nervous system, TA is generally considered the immediate precursor for OA. OA is synthesized from tyrosine by decarboxylation to tyramine and then subsequent β-hydroxylation to OA (Evans (1985) supra). The quantification of OA and its precursors (tyrosine and TA) in the nervous systems of two lepidopteran insects, *Trichoplusia ni* and *Manduca sexta*, support the idea that TA represents the immediate precursor for OA. There are some indications that TA has a functional role distinct from OA. Various studies indicate a possible role for TA as neurotransmitter or neuromodulator, in spite of being the immediate precursor of the well established neurotransmitter, OA.

Among the monoamines present in the insect nervous system functioning as neurotransmitters, OA is the only one specifically active in insects and other invertebrates but not in vertebrates. This makes OA, OA receptors and OA transporters desirable targets for pest control strategies. Even though specific OA uptake systems have been functionally described in both insect tissue and synaptosomal preparations, the OA systems are heretofore relatively uncharacterized at the molecular level. There is a need in the field for characterization of components of the OA transport system that may serve as targets for insecticides. The present invention provides a nucleic acid encoding an insect OA transporter and related embodiments useful for the identification of insecticides.

SUMMARY OF THE INVENTION

The present invention is directed to an isolated nucleic acid encoding a lepidopteran octopamine (DA)/tyramine (TA) transporter. In a preferred embodiment the nucleic acid is isolatable from *Trichoplusia ni*. In another preferred embodiment the isolated nucleic acid has the nucleotide sequence of SEQ ID NO: 1. In another preferred embodiment the isolated nucleic acid has a sequence encoding the amino acid of SEQ ID NO: 2.

The present invention further provides vectors comprising a nucleic acid encoding a lepidopteran OA/TA transporter. Host cells comprising the vectors are also provided.

In another embodiment, the present invention provides a recombinant lepidopteran OA/TA transporter, and host cells, oocytes, kits and compositions comprising a recombinant lepidopteran OA/TA transporter. Methods of identifying agonists and antagonists to a lepidopteran OA/TA transporter are also provided.

BRIEF DESCRIPTION OF THE DRAWINGS

FIG. 1 provides the nucleotide (SEQ ID NO: 1) and deduced amino acid (SEQ ID NO: 2) sequence of the OA/TA transporter. The first nucleotide and amino acid residue of the translational start are designated as position 1. The 5'-UTR (384 nt) and 3'-UTR (107 nt) are depicted in lower case letters and the ORF (2013 bp) is depicted in upper case letters. The deduced amino acid sequence is depicted in upper case italic letters. The positions of the translational start codon (ATG) are shown by the rectangle and the inframe stop codons (TAA) by the circles. The dashed line represents the polyadenylation signal.

FIG. 3 depicts the percent identities of partial octopamine transporter (pOAT) nucleic acid sequences obtained from eight species of moths or butterflies representing the seven major superfamilies within the higher Lepidoptera relative to that obtained from *T. ni* (*Trichoplusia* pOAT).

FIG. 6 depicts the percent identities of partial octopamine transporter (pOAT) amino acid sequences obtained from eight species of moths or butterflies representing the seven major superfamilies within the higher Lepidoptera relative to that obtained from *T. ni* (*Trichoplusia*pOAT).

DETAILED DESCRIPTION OF THE INVENTION

Figure 2:
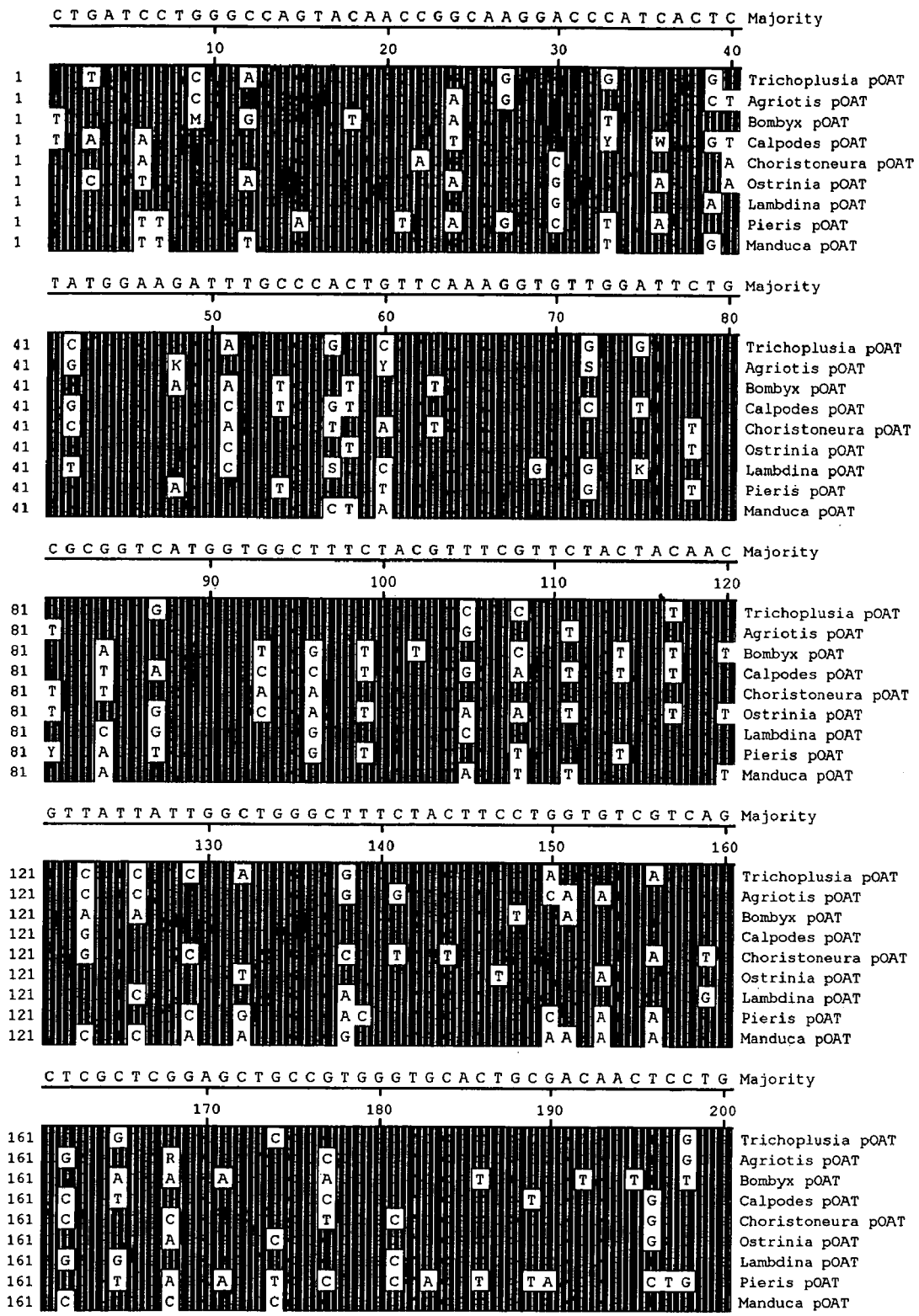
FIG. 2 depicts the alignment between partial octopamine transporter (pOAT) nucleic acid sequences obtained from eight species of moths or butterflies representing the seven major superfamilies within the higher *Lepidoptera* and that obtained from *Trichoplusia ni* (*Trichoplusia* pOAT). Abbreviations: *Agriotis*—black cutworm (*Agriotis epsilon*)of the superfamily Noctuoidea; *Bombyx*—silkmoth (*Bombyx mori*) of the superfamily Bombycoidea; *Calpodes*—Brazilian skipper (*Calpodes ethlius*) of the superfamily Hesperioidea; *Choristoneura*—Spruce budworm (*Choristoneura fumiferana*) of the superfamily Torticoidea; *Ostrinia*—cornborer (*Ostrinia nubilalis*) of the superfamily Pyraloidea; *Lambdina*—hemlock looper (*Lambdina fiscallaria*) of the superfamily Geometroidea; *Pieris*—cabbage white (*Pieris rapae*) of the superfamily Papilionoidea. *Manduca*—tomato hornworm (*Manduca cinquemaculata*) of the superfamily Bombycoidea. Majority: SEQ ID NO:21; *Trichoplusia*: SEQ ID NO:22; *Agriotis*: SEQ ID NO:23; *Bombyx*: SEQ ID NO:24; *Calpodes*: SEQ ID NO:25; *Choristoneura*: SEQ ID NO:26; *Ostrinia*: SEQ ID NO:27; *Lamdina*: SEQ ID NO:28; *Pieris*: SEQ ID NO:29; *Manduca*: SEQ ID NO:30.
Figure 2:
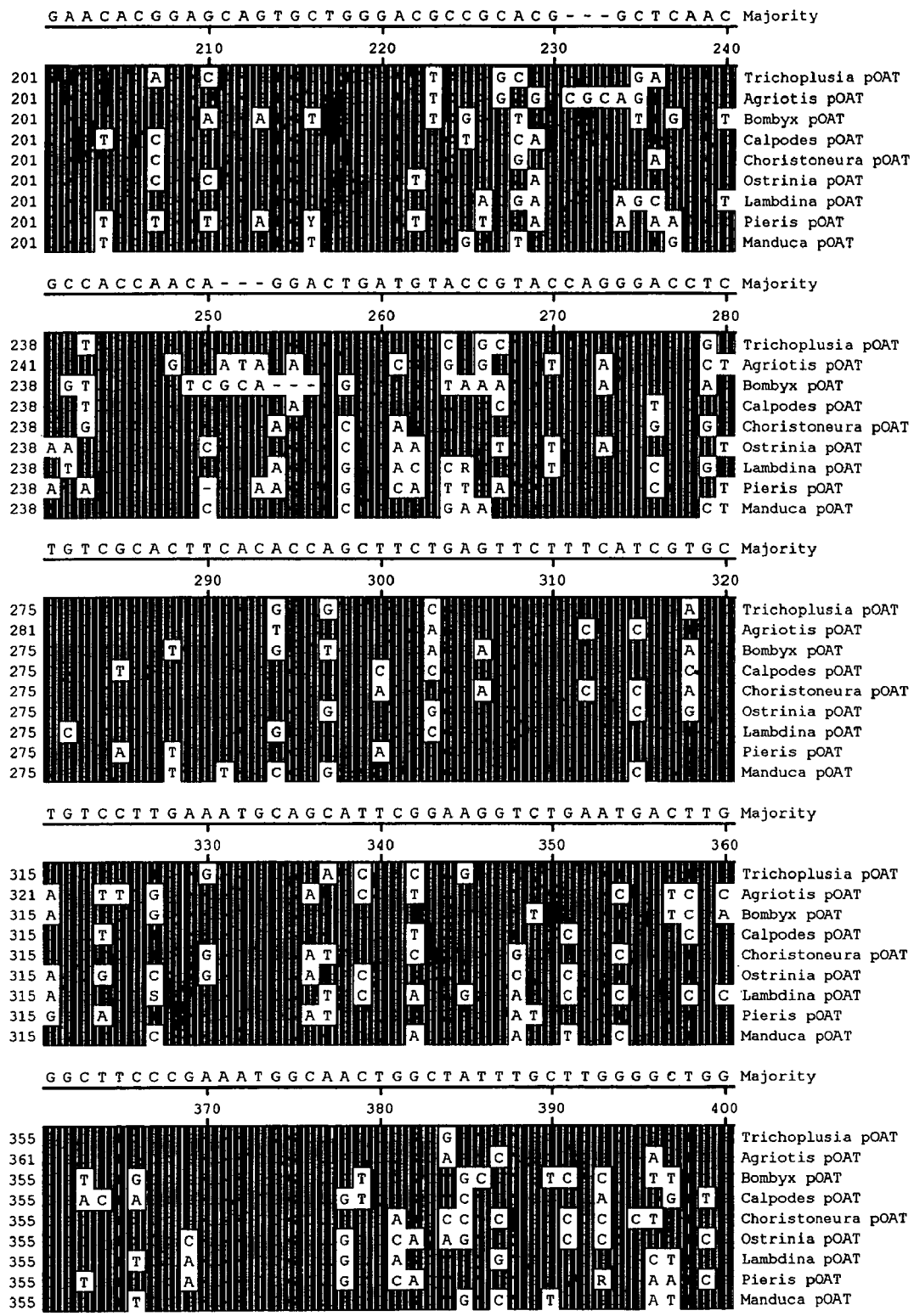
Figure 2:
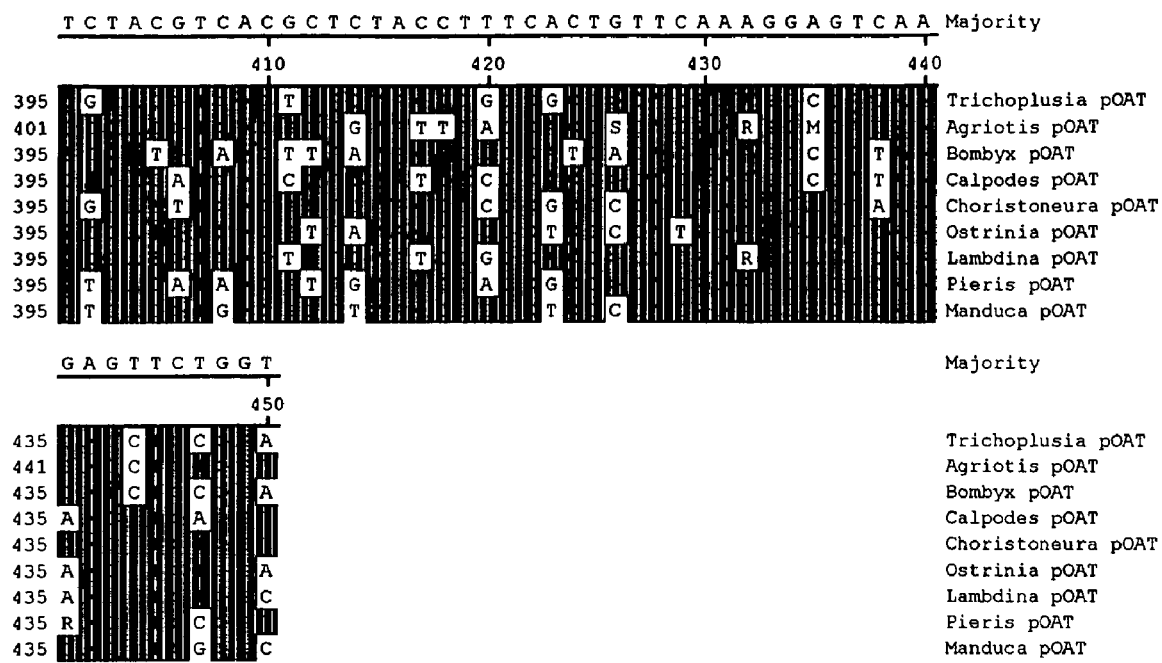

The present invention is directed to isolated nucleic acids encoding lepidopteran OA/TA transporters. An isolated nucleic acid encoding a lepidopteran OA/TA transporter is defined herein as a nucleic acid isolatable from an insect of the order lepidoptera and capable of encoding, under appropriate conditions, a functional OA/TA transporter. In a preferred embodiment, the nucleic acid is isolatable from caterpillars of the cabbage looper, *Trichoplusia ni* (*T. ni*). A functional OA/TA transporter is defined herein as a protein which, when expressed in a suitable host cell or membrane, transports OA and TA into the cell or across the membrane in a sodium-dependent and dose-dependent manner.

The isolated nucleic acid may be DNA or RNA, including cDNA and mRNA. In a preferred embodiment, the isolated nucleic acid has a sequence encoding the amino acid sequence set forth in FIG. 1 (SEQ ID NO: 2). The ordinarily skilled artisan, with the knowledge of the degeneracy of the genetic code, can determine DNA and RNA sequences that encode the amino acid sequence set forth in SEQ ID NO: 2. Further, the sequence may be selected to optimize expression in a particular host organism by using known preferred codons for the host organism of choice.

In another embodiment, the present invention provides isolated nucleic acids having at least about 60%, more preferably at least about 70%, at least about 75%, or at least about 80%, and most preferably at least about 90% or at least about 95%, sequence identity to the nucleic acid of SEQ ID NO: 1, wherein said nucleic acids encode a functional OA/TA transporter. Sequence identify is determined using the program Clustal W described by Higgins et al. (1994) *Nucleic Acids Res.* 22:4673 and may be calculated using the EMBL Nucleotide Sequence Database.

The present invention further provides nucleic acids capable of hybridizing under moderate or high stringency conditions to the complement of the nucleic acid of SEQ ID NO: 1 and capable of encoding a functional OA/TA transporter. Nucleic acid hybridization conditions are disclosed by Sambrook et al. (1989) Molecular Cloning—A Laboratory Press. Moderate stringency conditions are defined herein as about 50° C., 2×SSC, 0.1% SDS. High stringency conditions are defined herein as about 60° C., 0.1×SSC, 0.1% SDS.

In another embodiment, the present invention provides isolated nucleic acids having at least about 60%, more preferably at least about 70%, at least about 75%, or at least about 80%, and most preferably at least about 90% or at least about 95%, sequence identity to the nucleic acid of SEQ ID NO: 1, wherein said nucleic acids encode a functional OA/TA transporter. Sequence identify is determined using the program Clustal W described by Higgins et al. (1994) *Nucleic Acids Res.* 22:4673 and may be calculated using the EMBL Nucleotide Sequence Database (http://www.ebi.ac.uk/embl.html).

The present invention is further directed to vectors comprising the isolated nucleic acids of the present invention. In the vectors of the present invention, the nucleic acid encoding a lepidopteran OA/TA transporter is operably linked to suitable transcriptional and/or translational regulatory elements to effect expression of the OA/TA transporter in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and vectors into which the nucleic acid of the invention can be inserted are also commercially available. Recombinant viral vectors, including retrovirus, baculovirus, parvovirus and densovirus vectors are particularly preferred.

In a preferred embodiment the vector comprises a strong constitutive or inducible promoter operably linked to a nucleic acid encoding a lepidopteran OA/TA transporter. Suitable promoters are well known and readily available to one of ordinary skill in the art, and include for example, the polyhedrin promoter (Kitts et al., 1993, *BioTechniques*, 14:810), heat shock promoter (Stellar et al., 1985, *EMBO J.*, 4:167) and metallothionein promoter (Kaufman et al., 1989, *Cell* 59:359). Expression vectors can be constructed by well known molecular biological methods as described for example in Sambrook et al. (1989) Molecular Cloning: A Laboratory Manual Cold Spring Harbor Laboratory Press, Cold Spring Harbor, N.Y., or any of a myriad of laboratory manuals on recombinant DNA technology that are widely available. Expression vectors into which the nucleic acids of the present invention can be cloned under the control of a suitable promoter are also commercially available.

Another embodiment of the present invention provides host cells containing the vectors described above. The host cell may be procaryotic or eukaryotic, including bacterial, yeast, insect or mammalian. Insect and mammalian cells are preferred. Particularly preferred host cells include insect cell lines, including for example *Spodoptera frugiperda* cells. The host cells may be transformed, transfected or infected with the expression vectors of the present invention by methods well-known to one of ordinary skill in the art. Transfection may be accomplished by known methods, such as liposome mediated transfection, calcium phosphate mediated transfection, microinjection and electroporation. Permanently transformed insect cell lines are particularly preferred. For example, insect cell lines such as *Drosophila* cell line SH1 can be transformed with the expression vectors of the present invention by commercially available lipofectin (GIBCO-BRL) to provide permanently transformed cell lines expressing a functional OA/TA transporter. In a preferred embodiment, the vector is designed such that expression of the transporter is inducible.

Expression systems utilizing baculovirus vectors and insect host cells are also preferred. The use of baculoviruses as recombinant expression vectors to infect lepidopteran insect cells is known in the art and described for example by Luckow et al. (1988) *Bio/Technology* 6:47-55 and Miller (1988) *Ann. Rev. Microbiol.* 42:177-199. The baculovirus vectors generally contain a strong baculovirus promoter operably linked to a nucleic acid of the present invention such that the promoter directs expression of the lepidopteran OA/TA transporter. Baculovirus polyhedrin promoters such as the Autographa californica nuclear polyhedrosis virus polyhedrin promoter are preferred.

The baculovirus expression vectors of the present invention are made by inserting the nucleic acid encoding the lepidopteran OA/TA transporter downstream of the polyhedrin promoter in a baculovirus transfer vector, for example pBacPac8 available from Clontech or Bac-to-Bac available from Life Technologies. Baculovirus transfer vectors further contain flanking baculovirus sequences that allow homologous recombination between the transfer vector and baculovirus DNA during co-transfection. The transfer vector containing the nucleic acid of the invention and viral DNA are used to co-transfect insect cells. In a preferred embodiment the insect cells are *Spodoptera*. *Spodoptera frugiperda* cells including Sf9 are particularly contemplated. During co-transfection, homologous recombination results in the transfer of an expression cassette containing the polyhedrin promoter and the nucleic acid of the present invention to the polyhedrin locus of the viral DNA. The resulting recombinant virus is used to generate viral stocks by standard methods. Insect host cells are infected with the recombinant virus to produce insect cells expressing the OA/TA transporter.

The present invention is further directed to recombinant lepidopteran OA/TA transporter. The recombinant lepidopteran OA/TA transporter may be isolated in a membrane preparation or present in the cell membrane of the host cell in which it has been recombinantly produced. Whole cells and membrane preparations comprising the recombinant lepidopteran OA/TA transporter are particularly contemplated. Recombinant lepidopteran OA/TA transporter is useful, for example, to screen potential insecticides by specific binding assays or functional assays.

The present invention further provides a method of making a recombinant lepidopteran OA/TA transporter. Recombinant lepidopteran OA/TA transporter is made by transforming, transfecting or infecting a suitable host cell with an expression vector comprising a nucleic acid encoding a lepidopteran OA/TA transporter, culturing the host cell under conditions suitable for expression, and optionally recovering the recombinant lepidopteran OA/TA transporter. A suitable host cell is any cell in which the nucleic acid encoding the transporter can be expressed to provide a functional OA/TA transporter. In a preferred embodiment, the recombinant lepidopteran OA/TA transporter is made in insect cells, preferably *Spodoptera frugiperda* 9, by infecting the insect cells with a recombinant virus in which the nucleic acid of the invention is under the control of a polyhedrin promoter, and culturing the cells under conditions suitable for expression of the recombinant lepidopteran OA/TA transporter. In another preferred embodiment, the recombinant lepidopteran OA/TA transporter is made in permanently transformed cell lines as described hereinabove.

A functional OA/TA transporter can be identified by functional assays. For example, host cells expressing a putative recombinant OA/TA transporter are incubated with high $Na^+$ saline containing a labeled monoamine substrate and unlabeled or competitive substrate. The substrate is preferably OA or TA, or dopamine (DA), which is structurally similar to OA and TA. The label is preferably a radiolabel. Uptake is stopped by removing the solution and washing the cells with $Na^+$ free saline. The label accumulated by the cells is then measured as an indicator of substrate takeup by cells. A functional OA/TA transporter is capable of directing dose dependent uptake of DA, OA and TA into the cell. Uptake of each of these monoamines is competitively inhibited by the others.

The present invention further provides a method of identifying agents that agonize or antagonize the activity of the OA/TA transporter of the present invention. Agent that agonize the activity of the transporter are agents that facilitate the transport of a monoamine, including any of OA, TA and DA, into a cell expressing the transporter. Agents that antagonize the activity of the transporter are agents that inhibit the transport of the monoamine into a cell expressing the transporter. The method comprises contacting, in the presence of $Na^+$ ions, an oocyte, cell, or membrane expressing the DA/TA transporter with a putative agent and measuring transport of monoamine, such as OA, TA or DA, into the cell or across the membrane. Transporter activity may be measured by using a detectably labeled monoamine that is transported by the present transporter, such as OA, TA or DA. An increase in transport of the monoamine in the presence of the agent as compared to transport in the absence of the agent is indicative of an agonistic agent. A decrease in transport of the monoamine in the presence of the agent as compared to transport in the absence of the agent is indicative of an antagonistic agent. The agents identified by the present methods are potentially useful as insecticides against lepidoptera.

The present invention further provides an amphibian oocyte comprising a nucleic acid expressing a functional OA/TA transporter, and an amphibian oocyte expressing a functional OA/TA transporter. The oocytes are useful as a system for screening potential insecticides useful against insects of the order lepidoptera. Such oocytes can be made using the nucleic acids of the invention and methods known in the art. In a preferred embodiment, the oocyte is a *Xenopus laevis* oocyte. For example, expression vectors containing cDNA encoding OA/TA transporter under the control of a strong promoter can be injected into the nuclei of oocytes, after which oocytes are incubated for from one to several days, followed by assessment for presence of functional OA/TA transporter. Alternatively, mRNA can be synthesized in vitro from cDNA encoding the OA/TA transporter, and injected into oocytes, followed by assessment for presence of functional OA/TA transporters as described hereinabove.

Another embodiment of the present invention provides a composition comprising a recombinant lepidopteran OA/TA transporter in a cell membrane. The composition may be a membrane preparation, including a freeze dried membrane preparation, or an intact cell or oocyte expressing the functional lepidopteran OA/TA transporter. The composition is useful, for example, to screen for potential insecticides by functional or specific binding assays. The composition may further comprise appropriate carriers or diluents, including, for example, physiological buffers.

The present invention further provides a kit for identifying agonists and antagonists to a lepidopteran OA/TA transporter. The kit contains a first container containing a recombinant lepidopteran OA/TA transporter in a cell membrane. The membrane may be in the form of a membrane preparation, including a freeze dried membrane preparation, or an intact cell or oocyte expressing the functional lepidopteran OA/TA transporter. The kit of the present invention optionally further comprises monoamines known to be transported by the OA/TA transporter. The compositions and kits of the present invention are useful for identifying insecticides.

All references cited herein are incorporated in their entirety.

The following nonlimiting examples serve to further illustrate the present invention.

EXAMPLE 1

Materials and Methods

RNA Isolation

Different tissues (epidermis, fat body, brain, nerve cord, gonad, Malpighian tubules, midgut, hindgut, rectum, silk gland) from late instar larvae and *T. ni* adults (optic lobes, flight muscle) were collected, frozen in liquid nitrogen, and stored at −70° C. until use. Total RNA was isolated with TRIzol Reagent (Life Technologies) following manufacturer's instructions. The total RNA isolated from optic lobes was separated from the eye pigments, which co-precipitate with RNA, by spinning the total RNA through a Chroma spin-100, DEPC-H$_2$O column (Clontech). The RNA recovered from the column was dissolved in diethylpyrocarbonate (DEPC)-treated water. RNA was quantified by spectrophotometry and separated on a 1% agarose gel under denaturing conditions to check its integrity before use in RT-PCR or Northern analysis.

PCR Using Degenerate Primers and cDNA from *T. ni*:

The degenerate primers were designed from highly conserved regions found in the Na$^+$/ Cl$^-$ dependent neurotransmitter transporter protein family following the amino acid sequence for mammalian dopamine transporters (DAT1: GMPLFYME (SEQ ID NO:3); DAT2: WKGVKTSG (SEQ ID NO:4); DAT3: KVVWITAT (SEQ ID NO:5)) and GABA transporters (GABA1: NVWRFPY(SEQ ID NO:6); GABA2: SKWGKWICF (SEQ ID NO:7)) (Shafqat et al., (1993) *Mol. Endocrinol.* 7:1517). The upstream primers (DAT1 and GABA1) were located outside of the transmembrane (TM) domain 3, while the downstream primers (DAT2, DAT3, GABA2) were located outside of the TM domain 4. The neurotransmitter transporter-like fragments were amplified by PCR from first strand cDNA (2 µl) using various primer combinations: DAT1/DAT3, DAT1/DAT2, GABA1/DAT3 and DAT1/GABA2. The PCR mix (25 µl) contained: 0.2 mM dNTP's, 2.5 mM MgCl$_2$, 2 pmoles/µl degenerate primers and 2.5 U Taq DNA Polymerase (0.5 µl) (Life Technologies). The amplification was performed using 35 cycles of denaturation at 94° C. for 45 sec, annealing at 55° C. for 45 sec and elongation at 72° C. for 1 min. The denaturation step of the first cycle was 2 min long and the elongation step of the last cycle was 5 min (Perkin Elmer, DNA Thermal Cycler 480) (Sambrook et. al., (1989) Molecular Cloning—A Laboratory Manual. Cold Springs Harbor Laboratory Press. The PCR products were cloned in pCR-Script SK(+) (Stratagene) and several clones from each reaction were sequenced.

Nested Rapid Amplification of cDNA Ends (Nested RACE-PCR):

The nested RACE-PCR was performed using double stranded cDNA ligated into the pBK-CMV vector as the template. Two sets of nested primers, one at each end of the cDNA insert, were designed from the vector sequence. The upstream primers: BKRev (5' ACAGGAAACAGCTAT-GACCTTGAT 3'; SEQ ID NO:8) and T3+ (5' CCTCAC-TAAAGGGAACAAAAGCTG 3'; SEQ ID NO:9), flanked the cDNA at its 5' end while the downstream primers: BKFor (5'GTAAAACGACGGCCAGTGAATTGT3'; SEQ ID NO:10) and T7+ (5ACGACTCACTATAGGGCGAAT-TGG3': SEQ ID NO:11), flanked the 3' end of the cDNA. Two other sets of nested unique primers were designed from a 481 bp DNA fragment amplified in a previous PCR with degenerate primers. These were: For1 (5'ACCACTTTCCG-GAGCTCTTGAC3': SEQ ID NO:12) and For2 (5'CTTTGAACAGCGACAGGTAGAGAG3'; SEQ ID NO:13) facing upstream and Rev1 (5'ACATGGAGCT-TATCTTCGGACAGT3'; SEQ ID NO:14) and Rev2 (5'AGGGACCGATCACGCTCTGGAAG3'; SEQ ID NO:15) facing downstream. The first half of the cDNA containing the 5' end was amplified using BKRev and For1 primers and cDNA (0.5 µl) in the first round. The products amplified (1 µl out of 50 µl) were used as template for the nested PCR with T3+ and For2 primers. A similar approach was used to amplify the second half of the sequence, at the 3' end of the cDNA using, BKFor and Rev1 in the first reaction, and T7+ and Rev2 in the nested reaction. The PCRs were performed with high fidelity DNA polymerase, a mixture of Taq and Pwo DNA polymerases from the Expand Long Template PCR System (Boehringer Mannheim). The PCR mix contained: 0.4 pmoles primers, 3 mM MgCl$_2$, 350

μM dNTP's, 2.5 U (0.75 μl) enzyme in 1× buffer 3. The number of cycles for both rounds of amplification were 22 of denaturation at 94° C. for 45 sec, annealing at 65° C. for 45 sec. The elongation was done at 68° C. for 3 min 30 sec of the first 10 cycles and the elongation time increased with 20 sec per cycle for the last 12 cycles. The denaturation step of the first cycle was 2 min and the elongation step of the last cycle was 15 min (Perkin Elmer, DNA Thermal Cycler 480) (Sambrook et. al., 1989).

Reverse Transcriptase Polymerase Chain Reaction (RT-PCR)

First strand cDNA was synthesized from 3 μg total RNA isolated from: epidermis, fat body, brain, nerve cord, optic lobes, gonad, flight muscle, Malpighian tubules, midgut, hindgut, rectum and silk gland using Superscript II Reverse Transcriptase in the presence of 150 ng random primers, 500 μM dNTP's, 10 mM DTT and 1× first strand buffer (Life Technologies) for 10 min at 25° C. followed by 50 min at 42° C. Two μl of the cDNA synthesized was used as template for PCR amplification. The cDNA of interest originating from the OA/TAT mRNA was amplified by two unique primers (3 Utr/Rev6). The pair of primers used was selected so it would amplify different size products from cDNA versus genomic DNA (which is present as contaminant from RNA isolation). Different pairs of primers were first checked on genomic DNA to ensure that the primers encounter an intron. The PCR mix contained: 0.2 mM dNTP's, 2 mM MgCl$_2$, 0.3 pmoles primers and 2.5 U Platinum Taq DNA Polymerase (Life Technologies)/50 μl reaction. The PCR was performed using 35 cycles of denaturation at 94° C. for 30 sec, annealing at 62° C. for 30 sec and elongation at 72° C. for 50 sec. The denaturation step of the first cycle was 3 min long and the elongation step of the last cycle was 5 min (Gene Amp, PCR System 9700). One fifth of the PCR reaction (10 μl) was separated on a 1.2% agarose gel and the DNA fragments were detected by ethidium bromide staining (1 μg/ml ddH$_2$O) for 20 min, followed by 20 min destaining in ddH$_2$O.

To ensure that the cDNA synthesis as well as the PCR amplification was comparable in all the samples a ubiquitously expressed transcript, glyceraldehyde 3-phosphate dehydrogenase (G3PDH) was amplified from all the samples. Two unique primers were designed from the cDNA encoding G3PDH to amplify specific products. The downstream primer (5' CTTGTTTCTACATAAATTTATTCC 3'; SEQ ID NO:16) and the upstream primer (5' AACAACATT-TATCTCTACACTGCTA 3'; SEQ ID NO:17) were located in the 5' UTR and the 3'UTR, respectively. The internal control using the G3PDH primers was performed under the same conditions as those used for the samples, except the annealing temperature and elongation time were 58° C. and 2 min respectively.

Southern Analysis

The genomic DNA isolated from late instar *T. ni* larvae was digested (15 μg genomic DNA/reaction) with six different restriction enzymes (PstI, BamHI, XhoI, KpnI, BglII, SalI), ethanol precipitated and resolved on 0.8% agarose gel by electrophoresis (1.75V/cm). The restriction fragments distribution was detected by ethidium bromide staining (1 μg/ml in ddH$_2$O, 20 min.) and destaining (ddH$_2$O, 20 min). The DNA fragments were denatured by soaking the gel for 3 times for 15 min each in denaturing solution (1.5 M NaCl, 0.5M NaOH) and neutralized it by soaking it twice for 30 min each time in neutralizing solution (1.5 M NaCl, 1M Tris pH 7.4). The genomic DNA was then transferred by capillary action (20×SSC 3 M NaCl, 0.3M sodium citrate) to a Hybond-N nylon membrane (Amersham) and UV cross-linked to the membrane (CL-100 Ultraviolet Crosslinker, UVP). The blot was hybridized with a 800 bp DNA fragment previously amplify by PCR from genomic DNA using Rev7 and 3'UTR primers and labeled using random oligomers and [α-$^{32}$P]dCTP (Amersham). The PCR mix used to amplify the 800 bp fragment contained: 0.2 mM dNTP's, 2 mM MgCl$_2$, 0.3 pmoles primers and 2.5 U Taq DNA Polymerase (Life Technologies)/25 μl reaction. The amplification was performed using 35 cycles of denaturation at 94° C. for 30 sec, annealing at 62° C. for 30 sec and 50 sec elongation time. The denaturation step of the first cycle was 3 min and the elongation step of the last cycle was 5 min (Gene Amp, PCR System 9700). The DNA fragment used as probe did not contain any of the six restriction sites used to digest the genomic DNA. Hybridization of the membrane was done in QuikHyb Rapid Hybridization Solution (Stratagene) with 2×10$^6$ dpm/ml $^{32}$P-labeled probe at 65° C. for 3 hours. The membrane was washed twice for 15 minutes in low stringency conditions (2×SSC/0.1% SDS, room temperature) and once for 30 minutes in high stringency conditions (0.1×SSC/0.1% SDS, 60° C.) (Sambrook et. al., 1989). Lambda phage cut with HindIII was run as a marker on the gel and later hybridized as above with $^{32}$P labeled λ DNA for detection.

Northern Analysis

Total RNA (15 μg) isolated from different tissues (see RNA isolation) was resolved on a 1% agarose gel in the presence of 6.5% formaldehyde (1.5 V/cm), transferred to Hybond-N+ nylon membrane (Amersham) through capillary transfer (20×SSC) and UV cross-linked to the membrane. The RNA blot was then probed with a 2.2 kb DNA fragment encoding the open reading frame of OA/TAT. The 2.2 kb DNA fragment was amplified by PCR with 5'UTR and 3'UTR primers from cDNA (see 2.1 Cloning the OA/TAT cDNA into baculovirus) and labeled with [α-$^{32}$P]dCTP using random oligomers (Amersham). The hybridization was done in QuikHyb Rapid Hybridization Solution (Stratagene) with 2×10$^6$ dpm/ml probe at 65° C. for 3 hours. After hybridization the membrane was washed twice for 15 min each in low stringency conditions (2×SSC/0.1% SDS, at room temperature) and once for 30 min in high stringency conditions (0.1×SSC/0.1% SDS, at 60° C.) (Sambrook et. al., 1989). A 0.24-9.5 kb RNA ladder (5 μg) (Life Technologies) was run along with the RNA samples and hybridized with $^{32}$P-labeled λ DNA using the same conditions as above. The integrity and the concentration of the RNA on the membrane was checked by probing it with a DNA fragment encoding the 3' end of the G3PDH cDNA. The G3PDH fragment (550 bp) was amplified from cDNA using the downstream primer 5' AACAACATTTATCTCTACACT-GCTA 3' (SEQ ID NO: 17) and the upstream primer 5' GGCCAAGGTCATCCATGACAACTT 3' (SEQ ID NO:18). The PCR mix used contained: 2 mM dNTP's, 2 mM MgCl$_2$, 0.3 pmoles/μl primers, 0.35 μl cDNA and 2.5 U Taq DNA Polymerase in 1× buffer (Life Technologies). The PCR was performed using 37 cycles of denaturation at 94° C. for 30 sec, annealing at 62° C. for 30 sec and elongation 72° C. for 1 min 20 sec. The denaturation step of the first cycle was 3 min long and the elongation step of the last cycle was 5 min (Gene Amp, PCR System 9700). The G3PDH DNA fragment was labeled using random oligomers, [α-$^{32}$P]dCTP and used for hybridization as previously described.

Sequencing Procedure

The nested RACE-PCR products were cloned in the pGEM-T Easy Vector (Promega), producing the plasmids pGEM-T 1298 for the 5' end fragment and pGEM-T 1620 for the 3' end. Each of the two fragments were sequenced on one strand and the sequences used to design two unique primers that amplified the full open reading frame of the cDNA: 5'UTR-BamHI (5' GCGGATCCACGCACAGGAC-CATGAGAC 3'; SEQ ID NO:19) and 3'UTR-KpnI (5' CGGGTACCGAAGCGCCTATTTCTGACT 3'; SEQ ID NO:20). BamHI and KpnI represent the two restriction sites built into the primers. Using 5' Utr-BamHI and 3' Utr-KpnI primers with first strand cDNA the full open reading frame was amplified as one piece. A high fidelity enzyme mixture of Taq and Pwo DNA polymerases: (Expand Long Template PCR System-Boehringer Mannheim) was used to minimize incorporation errors (see Cloning the OA/TAT cDNA into baculovirus). This DNA fragment encoding the whole ORF was cloned into the pGEM-T Easy Vector producing the plasmid pGEM-T2204 using the BamHI and KpnI restriction sites. pGEM-T2204 was used for sequencing the ORF of OA/TAT cDNA on both strands. The sequencing approach used was one of walking along the sequence using multiple primers and then overlapping the sequences. The 5' and 3' untranslated regions were sequenced on both strands from pGEM-T1298 and pGEM-T1620.

BLAST Search

BLAST search and amino acid sequence comparison (Lasergene, software package) were used to identify neurotransmitter transporter-like fragments from the PCR products amplified with degenerate primers or the PCR products obtained from nested RACE-PCR. BLAST was also used to determine the orientation and the position of the amplified products compared to the entire cDNA sequence.

Constructing the Recombinant Baculovirus Containing Octopamine/Tyramine Transporter cDNA Cloning the OA/TAT cDNA into Baculovirus The cDNA fragment (2204 bp) encoding the complete open reading frame of OA/TAT was amplified by PCR from first strand cDNA using two unique primers: 5'UTR-BamHI, 3'UTR-KpnI. The PCR mix contained: 1.5 µl first strand cDNA, 0.3 pmoles primers, 3 mM $MgCl_2$, 350 µM dNTP's, 2.5 U (0.75 µl) enzyme mix (Taq and Pwo DNA polymerases) in 1× buffer 3 (Expand Long Template PCR System; Boehringer Mannheim). The PCR amplification was performed using 37 cycles of denaturation at 94° C. for 30 sec, annealing at 65° C. for 30 sec and elongation at 68° C. for 2 min 10 sec of the first 10 cycles and for the last 27 cycles the elongation increased with 20 sec per cycle. The denaturation step of the first cycle was 2 min 30 sec and the elongation time of the last cycle was 15 min long (Gene Amp, PCR System 9700). The restriction enzyme sites built into the primers (BamHI, KpnI) and subsequently into the cDNA fragment were used to clone it into the pFastBac1 transfer vector under the control of the polyhedrin promoter (Life Technologies). pFastBac1 also contains a mini-Tn7 transposable element used to transpose the foreign gene to the mini-attTn7 attachment site on a baculovirus shuttle vector (bacmid). The transposition requires the presence of a helper plasmid (pMON7124) already present in the DH-10 Bac *E. coli* cell line (Life Technologies). The successful transposition disrupts the lacZa gene present in the bacmid giving blue-white color selection. Individual colonies containing the recombinant bacmid were grown and the bacmid isolated through a high molecular weight DNA method (Bac-to-Bac manual, Life Technologies). The bacmid DNA was then used to transfect Sf9 insect cells, and recombinant baculovirus particles collected in the cell supernatant.

Transfection of Sf9 Cells with Recombinant Baculovirus

Sf21 cells were plated at $9 \times 10^5$ cells/well in a 6-well plate, one hour prior to transfection (2 ml TC-100) (Life Technologies). The transfection mixture (5 µl bacmid diluted in 100 µl serum and antibiotics-free TC-100 medium mixed with 6 µl CellFectin Reagent diluted in 100 µl serum and antibiotics-free TC-100) was incubated at room temperature for 30 min. After the incubation, 0.8 ml serum and antibiotics-free TC-100 was added to the transfection mixture and overlaid onto the cells previously washed with serum and antibiotics-free TC-100. The cells and the transfection mixture were incubated for 5 hours at 27° C. Then, the transfection mixture was removed and replaced with 2 ml of fresh TC-100. The cells were incubated for 72 hours at 27° C. The medium containing the virus was collected, centrifuged for 10 min at 500 g to remove the floating cells and stored at 4° C., in the dark with 12% FBS.

Viral Plaque Assay and Virus Amplification

The virus collected from the transfection was first titered via plaque assay and then amplified. For the plaque assay, $4 \times 10^5$ Sf9 cells/well were plated in a 6-well plate and left to adhere overnight at 27° C. Serial dilutions ($10^{-2}$ to $10^{-6}$ or $10^{-7}$) of the viral stock were made in 1 ml Grace's Medium and added to the cells after the old medium was removed. During the viral infection the virus was mixed every 10-15 min for 1 hour. Then, the virus containing medium was removed and the cells were covered with 3 ml/well plaquing overlay (0.5% agarose in Grace's Medium) equilibrated at 42° C. Once the overlay solidified, the plates were incubated in a high humidity atmosphere at 27° C. until the individual plaques formed (10-14 days). The titer expressed in pfu/ml, was calculated from the number of plaques formed at a particular dilution.

The virus collected from the transfection was amplified in Sf9. First, Sf9 cells seeded at $2-4 \times 10^5$ cells/ml density in T25 flasks were incubated at 27° C. until they reached 60-70% confluence. Then, the medium was removed and replaced with 1 ml fresh medium containing the necessary virus to give a Multiplicity of Infection (MOI) of 0.1 to 1. The virus overlaying the cells was mixed every 10-15 min for 1.5 hours and then 9 ml of fresh medium was added to the flask and the cells were incubated at 27° C. for 72 hours. The virus was harvested as described above (see Transfection of Sf9 with recombinant baculovirus).

Expression Studies of Octopamine/Tyramine Transporter in Insect Cells

Viral Infection

The optimal infection conditions for Sf21 cells were determined by varying the MOI (0.5; 1; 1.5; 2) and the number of cells seeded per well ($1 \times 10^5$; $1.5 \times 10^5$; $2 \times 10^5$). The best working combination was $2 \times 10^5$ cells/well infected at a MOI of 0.5. Twelve hours prior to infection the Sf21 cells were seeded in a 12-well plate at a density of $2 \times 10^5$ cells/well. The next day, the old medium was removed and the cells were covered with 500 µl medium containing 22.2 µl viral stock ($0.9 \times 10^7$ pfu/ml). The virus was mixed every 10-15 min for 1 hour and then another 1 ml of fresh medium was added to the well. The cells were assayed for transport activity 44-48 hours post-infection.

Transport Assays

The insect cells expressing OA/TAT were assayed for protein activity 44-48 hours post-infection. The medium was removed from the cells and each well was washed with one volume (1 ml) of physiological saline ($MgCl_2$ 11.2 mM, $MgSO_4$ 11.2 mM, NaCl 53.5 mM, $NaH_2PO_4$ 7.3 mM, KCl 55.0 mM and sucrose 76.8 mM) and incubated for an hour in a second volume of physiological saline. The physiological saline was then removed and the cells were washed once with high $Na^+$ saline (1 ml) ($MgCl_2$ 11.2 mM, $MgSO_4$ 11.2 mM, NaCl 92.7 mM, $NaH_2PO_4$ 7.3 mM and K-gluconate 55 mM). Then, the cells were exposed to 500 µl high $Na^+$ saline containing 0.3 µM $^3$H-dopamine (5 or 6 µl of $^3$H-dopamine with specific activity of 33.8 or 40.0 Ci/mmol, equivalent to 30.3 or 25 nmol dopamine/ml, respectively) (NEN Life Sciences Products, Inc.). The 500 µl solution also contained unlabeled DA or competitive substrate/inhibitor as required by each experiment. The cells were exposed to these solutions for 3 min. The uptake was stopped by removing the radio-labeled solution and then washing the cells three times (2 ml/well/wash) with $Na^+$ free saline. The plate was air dried and the radio-label ($^3$H-DA) accumulated by the cells was extracted for 1 hour with 500 µl 70% ethanol, on a gyratory shaker. An aliquot of 400 µl was then removed from each well, added to 10 ml scintillation fluid (Ready Safe, Beckman) and the radioactivity counted. All washes and incubations were done at 26-27° C. All the solutions containing amines were made with ice cold salines and kept on ice until 5 min before use, when they were warmed to 27-28° C.

The concentration of the $^3$H labeled dopamine was checked by HPLC with electrochemical detection and found to be the concentration claimed by the company (30.3 nmol/ml).

Neither $^3$H-labeled octopamine (OA) nor tyramine (TA) is commercially available. Because dopamine (DA) is structurally similar to OA and TA and commercially available at a reasonable price (NEN Life Sciences Products, Inc.), $^3$H-DA was used as OA/TAT's substrate for all expression and pharmacological studies.

Determining the $K_m$ for Dopamine (DA)

In order to determine the $K_m$ for DA its concentration per well was increased from 0.1 µM to 20 µM (0.1; 0.2; 0.3; 0.6; 0.8; 1; 2; 4; 6; 8; 10; 20). The first two wells were dosed with 1.67 µl (0.1 µM) and 3.34 µl (0.2 µM) $^3$H-DA, respectively. The rest of the wells were dosed with 5-6 µl $^3$H-DA (0.3 µM) plus unlabeled DA to give the concentrations listed above. The data were graphed and analyzed using Sigma Plot graphing program. The substrate $K_m$ and the $V_{max}$ were determined by nonlinear least-squares fits (Sigma Plot) using the equation y=a*x/b+x or its equivalent $V=v_{max}*[S]/K_m+[S]$ in which y, v=transport velocity, a, $V_{max}$=maximal velocity, x, [S]=substrate concentration, b, $K_m$=Michaelis-Menten constant.

Competitive Inhibition Studies

The inhibition curves for TA, OA and norepinephrine (NE) were determined using different concentration ranges. The concentration range of unlabeled TA, OA was from 0.1 to 20 µM and the concentration range for NE was from 5 to 100 µM. TA's concentration was: 0.1; 0.2; 0.3; 0.5; 0.75; 1.0; 1.5; 2.5; 5.0; 10.0; 20.0 µM. OA's concentration was: 0.1; 0.2; 0.3; 0.6; 1.0; 2.0; 4.0; 6.0; 8.0; 10.0; 20.0 µM and NE's concentration was: 2.0; 5.0; 10.0; 15.0; 20.0; 25.0; 30.0; 40.0; 60.0; 80.0; 100.0 µM. The uptake of $^3$H-DA (0.3 µM) in the presence of the unlabeled monoamines was determined as mentioned above (Transport Assay). Other naturally occurring biogenic amines or their metabolites (epinephrine, synephrine, serotonin, histamine, tryptamine, 2-phenylethylamine, ephedrine, pseudoephedrine) and potential competitive inhibitors (imipramine, desipramine, nomifensine, GRB12909, riluzole, chlorpromazine) were tested at 10 µM except riluzole (100 µM). The $IC_{50}$ (concentration of inhibitor producing 50% inhibition) values were determined from individual Hill plots (double logarithmic scale of concentration of inhibitor against $I/I_{max}-I$ where I is inhibition and $I_{max}$ is maximal inhibition). The $K_i$ (inhibition constant) values were calculated based on Cheng and Prusoff's prediction (Cheng and Prusoff, 1973) using the equation: $IC_{50}=K_i(1+[S]/K_m$ where [S] is substrate concentration, $K_m$=Michaelis-Menten constant for the substrate.

$Na^+$, $Cl^-$ Substitution

To determine the cation requirements of OA/TAT, $Na^+$ (100 mM) ions were replaced with following monovalent cations: $K^+$, $Li^+$, choline$^+$ or $NMG^+$ [100 mM] the ionic composition of the salines are as follows:

| CATION REPLACEMENT SALINES Total [anion] 177.4 mM [$Na^+$] or its [substituted cation] 100 mM Osmotic pressure 355 mOsm | | |
| --- | --- | --- |
| Saline type | Salt | Concentration (mM) |
| CONTROL SALINE | $MgSO_4$ | 22.4 |
|  | NaCl | 92.7 |
|  | $NaH_2PO_4(H_2O)$ | 7.3 |
|  | Potassium glutamate | 55.0 |
| CHOLINE SALINE | $MgSO_4$ | 22.4 |
|  | Choline chloride | 92.7 |
|  | $KH_2PO_4$ | 7.3 |
|  | Potassium glutamate | 55.0 |
| LITHIUM SALINE | $MgSO_4$ | 22.4 |
|  | LiCl | 92.7 |
|  | $KH_2PO_4$ | 7.3 |
|  | Potassium glutamate | 55.0 |
| NMG SALINE | $MgSO_4$ | 22.4 |
|  | NMG | 92.7 |
|  | $KH_2PO_4$ | 7.3 |
|  | Potassium glutamate | 55.0 |
| POTASSIUM SALINE | $MgSO_4$ | 22.4 |
|  | KCl | 92.7 |
|  | $KH_2PO_4$ | 7.3 |
|  | Potassium glutamate | 55.0 |

Similarly, to determine anion requirements of OA/TAT, $Cl^-$ (92.7 mM) ions were substituted with following anions: gluconate, citrate, iodide, bromide, nitrate, aspartate, phosphate, sulfate, carbonate and glutamate. The first set of salines maintained the concentration of the anion tested at 92.7 mM while the second set of salines contained variable anion concentration (50 to 100 mM).

Composition of the multiple-anion salines used in $Cl^-$ substitution experiments were as follows.

| B. ANION REPLACEMENT SALINES 1. Multiple-anion salines containing 92.7 mM $Cl^-$ or its substituted anion Total [anion] 177.4 mM Osmotic pressure 355 mOsm | | |
| --- | --- | --- |
| Saline type | Salt | Concentration (mM) |
| CONTROL SALINE | $MgSO_4$ | 22.4 |
|  | NaCl | 92.7 |
|  | $NaH_2PO_4(H_2O)$ | 7.3 |

-continued

B. ANION REPLACEMENT SALINES
1. Multiple-anion salines containing 92.7 mM Cl⁻ or
its substituted anion
Total [anion] 177.4 mM
Osmotic pressure 355 mOsm

| Saline type | Salt | Concentration (mM) |
|---|---|---|
| | Potassium glutamate | 55.0 |
| ASPARTATE SALINE | $MgSO_4$ | 22.4 |
| | Sodium aspartate | 92.7 |
| | $NaH_2PO_4(H_2O)$ | 7.3 |
| | Potassium glutamate | 55.0 |
| BROMIDE SALINE | $MgSO_4$ | 22.4 |
| | NaBr | 92.7 |
| | $NaH_2PO_4(H_2O)$ | 7.3 |
| | Potassium glutamate | 55.0 |
| CITRATE SALINE | $MgSO_4$ | 22.4 |
| | Sodium citrate ($H_2O$) | 92.7 |
| | $NaH_2PO_4(H_2O)$ | 7.3 |
| | Potassium glutamate | 55.0 |
| GLUCONATE SALINE | $MgSO_4$ | 22.4 |
| | Sodium gluconate | 92.7 |
| | $NaH_2PO_4(H_2O)$ | 7.3 |
| | Potassium glutamate | 55.0 |
| GLUTAMATE SALINE | $MgSO_4$ | 22.4 |
| | $NaH_2PO_4$ | 7.3 |
| | Sodium glutamate | 92.7 |
| | Sucrose | 55.0 |
| 'SUCROSE SALINE' | $MgSO_4$ | 7.2 |
| | $Na_2HPO_4$ | 7.3 |
| | $Na_2SO_4$ | 15.2 |
| | Sodium glutamate | 55.0 |
| | Sucrose | 92.7 |
| IODIDE SALINE | $MgSO_4$ | 22.4 |
| | NaI | 92.7 |
| | $NaH_2PO_4(H_2O)$ | 7.3 |
| | Potassium glutamate | 55.0 |
| NITRATE SALINE | $MgSO_4$ | 22.4 |
| | $NaNO_3$ | 92.7 |
| | $NaH_2PO_4(H_2O)$ | 7.3 |
| | Potassium glutamate | 55.0 |
| PHOSPHATE SALINE | Na2HPO4 | 50.0 |
| | KH2PO4 | 42.7 |
| | Magnesium gluconate | 55.0 |
| SULPHATE SALINE | $MgSO_4$ | 42.7 |
| | $Na_2SO_4$ | 50.0 |
| | Potassium glutamate | 55.0 |

All these salines were designed to have a major sodium salt containing Cl⁻ or the anion substituting for Cl⁻. To bring the total anion concentration of the salines to 177.4 mM, all salines except the glutamate, sulphate, phosphate salines contained: $MgSO_4$ (22.4 mM), $NaH_2PO_4$ or $KH_2PO_4$ (7.3 mM) and K-glutamate (55 mM). The glutamate saline contained sucrose (55 mM) instead of K-glutamate, the sulphate saline contained Na2SO4 (50 mM), MgSO4 (42.7 mM) and the phosphate saline contained two phosphate salts ($Na_2HPO_4$: 50 mM, $KH_2PO_4$: 42.7 mM) and Mg-gluconate (55 mM) instead of K-glutamate. The saline used to determine the uptake background levels caused by the presence of low levels of sulfate, phosphate and glutamate in all salines described above contained: $MgSO_4$ (22.4 mM), $Na_2HPO_4$ (7.3 mM), $Na_2SO_4$ (15.2 mM), K-glutamate (55 mM) ('sucrose saline'). The pHs of all these salines were adjusted to 7 with KOH. The osmotic pressure of all these salines was brought to 350 mOsm with sucrose.

Composition of the single-anion salines used in Cl⁻ substitution experiments were as follows:

2. Single-anion salines containing 50–100 mM Cl⁻ or
its substituted anion
Osmotic pressure 350 mOsm

| Saline type | Salt | Concentration (mM) |
|---|---|---|
| CONTROL SALINE | $MgSO_4$ | 22.4 |
| | NaCl | 92.7 |
| | $NaH_2PO_4(H_2O)$ | 7.3 |
| | Potassium glutamate | 55.0 |
| Cl⁻ (100 mM) SALINE | NaCl | 100.0 |
| | Sucrose | 150.0 |
| $NO_3^-$ (100 mM) SALINE | $NaNO_3$ | 100.0 |
| | Sucrose | 150.0 |
| $SO_4^{2-}$ (50 mM) SALINE | $Na_2SO_4$ | 50.0 |
| | Sucrose | 200.0 |
| $SO_4^{2-}$ (75 mM) SALINE | $Na_2SO_4$ | 50.0 |
| | $MgSO_4$ | 25.0 |
| | Sucrose | 150.0 |
| $H_2PO_4^-/HPO_4^{2-}$ (50 mM) SALINE | $Na_2HPO_4$ | 50.0 |
| | Sucrose | 200.0 |
| $H_2PO_4^-/HPO_4^{2-}$ (75 mM) SALINE | $Na_2HPO_4$ | 25.0 |
| | $NaH_2PO_4(H_2O)$ | 50.0 |
| | Sucrose | 175.0 |
| $HCO_3^{2-}/CO_3^{2-}$ (50 mM) SALINE | $Na_2CO_3$ | 50.0 |
| | Sucrose | 200.0 |
| $HCO_3^{2-}/CO_3^{2-}$ (75 mM) SALINE | $Na_2CO_3$ | 25.0 |
| | $NaHCO_3$ | 50.0 |
| | Sucrose | 175.0 |
| GLUTAMATE SALINE | Sodium glutamate | 100.0 |
| | Sucrose | 150.0 |
| GLUCONATE SALINE | Sodium gluconate | 100.0 |
| | Sucrose | 150.0 |

All these salines contained only Cl⁻ or a single type anion substituting for Cl⁻, all as sodium salts. The anion concentrations of salines in this set were: Cl⁻ (100 mM); $NO_3^-$ (100 mM); $SO_4^{2-}$ (50 mM, 75 mM); $HPO_4^{2-}/H_2PO_4^{-0}$ (50 mM, 75 mM); $CO_3^{2-}/HCO_3^-$ (50 mM, 75 mM); glutamate⁻ (100 mM); gluconate⁻ (100 mM). The pHs were adjusted to 7 with KOH, $H_3PO_4$ or $CO_2$. The osmotic pressure of all these salines was brought to 350 mOsm with sucrose.

Chemicals Used in Kinetic and Pharmacological Studies

Chemicals were obtained from (supplier: chemical [catalogue #]): Research Biochemicals Incorporated (RBI) Natick, Mass. 01760: Nomifensine [N-123]; Sigma-Aldrich, St. Louis, Mo. 63178-9916: (−)-Arterenol ([−]-Norepinephrine) [A-9512], Desipramine [D-3900], (−)-ψ-Ephedrine [E-9626], Histamine [H-7250], 5-Hydroxytryptamine (Serotonin) [H-9523], 3-Hydroxytyramine (Dopamine) [H-8502], Imipramine [I-7379], DL-Octopamine [O-0250], β-Phenylethylamine [P-6513], (±)-Synephrine [S-0752], Tryptamine [T-9628], Tyramine [T-2879]; Tocris Cookson Ballwin, Mo. 63011: GBR 12909 [0421]; Mann Research Laboratories: Ephedrine; NEN Life Science Products, Inc. Boston, Mass. 02118: Dihydroxyphenylethylamine, 3,4-[7-³H]-(³H-dopamine) [NET-131] at a radioactive concentration of 1.0 mCi/ml and specific activity of 30.8 and 40.0 Ci/mmol.

EXAMPLE 2

Molecular Characterization of the Octopamine/Tyramine Transporter

As a first step in cloning monoamine transporters, five degenerate primers (two upstream: DAT1, GABA1 and three downstream: DAT2, DAT3, GABA2) were designed from highly conserved regions of the Na⁺/Cl⁻ dependent neurotransmitter transporter family of proteins (Shafqat et al.,(1993) *Mol. Endocrinol.* 7:1517), following the amino acid sequence of dopamine transporters (DAT primers) or GABA transporters (GABA primers). The primers were designed to amplify the region in between the third transmembrane (TM) domain and fourth TM domain. The first strand cDNA synthesized with random hexamers from total head RNA was used as template for PCR. GABA1/DAT3 primers amplified a 612 bp DNA fragment that shares up to 45% identity to other cloned serotonin transporters (SERTs). DAT1/DAT3 primers amplified a 481 bp DNA fragment that shares up to 37% and 40% identity to the mammalian norepinephrine transporters (NETs) and dopamine transporters (DATs), respectively. DAT1/DAT2 primers amplified a 450 bp DNA fragment that shares up to 20% identity to other SERTs. The two SERT-like fragments (612 bp and 450 bp) do not share any significant similarity suggesting that they are either part of different transporters or the primers amplified different parts of the same protein. DAT1/GABA2 primers did not amplify any relevant fragments.

Two of the fragments described above (612 and 481 bp fragments) were used as probes in library screening. The 612 bp SERT-like fragment was used to screen $4.5 \times 10^5$ phages from an amplified *T. ni* head cDNA library and $5 \times 10^5$ phages from a similar primary library. The 481 bp NET-like fragment was used to screen $5 \times 10^5$ phages from the same amplified library. Neither one of the probes yielded any positive clones suggesting that the frequency of the cDNAs encoding for monoamine transporters was extremely low in the cDNA library. Therefore an alternative method was utilized for subsequent library screening which is based on PCR detection of target sequences in ordered arrays of library aliquots Israel (1995) supra. Each of the DNA fragments described above was identified and traced via PCR screening up to tertiary screening for 450 bp SERT-like fragment, secondary screening for 612 bp SERT-like fragment and primary screening for 481 bp NET-like fragment. Contrary to the expectation of the phage number containing the monoamine transporter cDNAs increasing, their number decreased with the number of passages. Therefore, the PCR screening results suggest that the phage containing the monoamine transporters have replicative disadvantages compared to the rest of the phages in the library. Most screening techniques are based one way or another on increasing the number of phages through replication steps. The only approach that does not involve phage replication is the RT-PCR based approach where cDNA obtained by reverse transcription from mRNA is used as template for PCR. With this approach the cDNAs encoding monoamine transporters is found at the same relative levels as their transcripts.

Cloning a cDNA that Encodes an Octopamine/Tyramine Transporter

Due to the low copy number and the defective replicative properties of the phages containing monoamine transporter cDNAs suggested by the results of previous screening techniques, RT-PCR based approach was used. Based on the known sequence of the 481 bp fragment, two sets of nested primers were designed to amplify the whole cDNA through a nested-RACE PCR approach. The primers were designed so that the products from both directions would overlap on the known 481 bp DNA fragment. To ensure that the nested-RACE PCR products contained the 481 bp sequence and therefore were part of the same cDNA, the nested-RACE PCR products were transferred to a Hybond N nylon membrane and probed with $^{32}$P-labeled 481 bp fragment. Two DNA fragments, one of 1620 bp at the 3' end and the other of 1298 bp at the 5'end of the cDNA were amplified and hybridized with the 481 bp fragment. They were both cloned and sequenced. The resulting plasmids are designated pGEM-T1298 and pGEM-T1620. BLAST search and amino acid comparison on the sequences reconfirmed the identity of the two pieces as being part of a cDNA encoding a NET-like transporter. Two unique primers flanking the ORF were designed to amplify the entire ORF of the cDNA in one piece (pGEM-T2204).

Characterization of Octopamine/Tyramine Transporter cDNA and its Gene Copy Number The sequence of 2504 bp cDNA amplified by PCR was analyzed and a single large ORF of 2013 bp was found which encodes a potential 670 amino acid protein. Of three potential start sites downstream of an in-frame stop codon at position −257 (FIG. 1, SEQ ID NO:1), the translational start shown at position 1 was predicted on the basis of a good agreement between the sequence context of this site and the consensus sequence for the initiation of translation predicted by Kozak, (1987) *Nucleic Acids Res.* 15:8125. The same start codon was also predicted when the OA/TAT cDNA sequence was analyzed using the 'Signal' utility within the PC/GENE sequence analysis program (IntelliGenetics, Inc.). The stop codon (TAA) is followed by a polyadenylation site (AATAAA) and a poly (A$^+$) tail. Southern blot analysis showed a single hybridizing band for each of the restriction enzymes used. The digested genomic DNA bound the $^{32}$P-labeled 800 bp intron-exon fragment as follows: PstI 6.2 kb; BamHI 14.5 kb; XhoI 12.5 kb; KpnI 14 kb; BglII 3.8 kb; SalI 14.8 kb.

Characterization of Octopamine/Tyramine Transporter Protein

The deduced amino acid sequence from the OA/TAT cDNA sequence (FIG. 1, SEQ ID NO:2) indicates an ORF of 670 amino acids constituting a protein of 74,645 Da molecular weight (DNA Star Software). Hydrophobicity analysis of the amino acid sequence suggests the presence of 12 potential transmembrane helices. The lack of an identifiable signal sequence suggests that both NH$_2$— and —COOH terminals are located on the cytoplasmic face.

The deduced amino acid sequence of OA/TAT shares up to 51% identity to the cloned mammalian monoamine transporters as determined by Clustal W-mp Multiple Sequence Alignment described by Higgins et al. (1994) Nucleic Acids Res 22:4673. Among those that share the highest degree of identity with OA/TAT, are: mouse NET (50.4%), human DAT (49.8%), frog ET (49.5%) and mouse SERT (45.4%). The most conserved regions are the TM domains while the most variable ones are at the NH$_3^+$ terminal. The amino acid sequence also reveals possible function/regulation sites or motifs as follows: a heptan leucine zipper motif (L-x(6)-L-x(6)-L-x(6)-L) present in the second TM (AA143 to AA164); two N-glycosylation sites (N-{P}-[ST]-{P}) on the second large extracellular loop (N240, N243) and phosphorylation sites for three different enzymes. The phosphorylation sites for protein kinase C (PKC)([ST]-x-[RK]) are: S39, T51, S59, S95 in the NH$_2$— terminal region, S308 between TM domain 4 and TM domain 5 and T635, S663 on the COO$^-$-terminal end. There is one tyrosine kinase (TyrK) phosphorylation site ([RK]-x(2,3)-[DE]-x(2,3)-Y): Y38 on NH$_2$-terminal and one cAMP-dependent protein kinase (cAMP PK) phosphorylation site ([RK](2)-x-[ST]: S551 between TM domain 10 and TM domain 11. In the above consensus patterns, the symbols represent: { } residues not allowed, x all residues allowed, [ ] residues allowed and the bold residue is the site itself. Based on the model predicting both amino and carboxy termini located on the inside of the membrane, all the phosphorylation sites indicated above would be present inside the cell and all the glycosylation sites would be found on extracellular loops.

Tissue Distribution of Octopamine/Tyramine Transporter mRNA

Distribution of the OA/TAT mRNA was evaluated by both Northern analysis and RT-PCR analysis from total RNA isolated from three neural tissues (brain, ventral nerve cord, optic lobes) and nine non-neural tissues (fat body, epidermis, silk gland, gonad, flight muscle, Malpighian tubules, midgut, hindgut, rectum). Northern analysis shows the presence of OA/TAT transcripts in optic lobes tissue. The optic lobes lane contains two different size RNAs: 7.65 kb and 5.25 kb, complementary to the OA/TAT cDNA. A G3PDH cDNA fragment used to assess the integrity of RNA loaded on each lane, binds to one massive band or two very similar in size, of approximately 1.44 kb. The results show the integrity of the resolved RNA is good in each of the lanes.

To confirm and potentially extend the information revealed by the Northern blot analysis, the tissue distribution of OA/TAT mRNA was studied by RT-PCR, a more sensitive technique than Northern analysis. RT-PCR was done using the same RNA samples as used for Northern blot analysis, so the results could be compared. The cDNA encoding for OA/TAT was amplified by PCR using two OA/TAT cDNA sequence specific primers. The OA/TAT cDNA and implicitly the OA/TAT transcripts were present in all three neural tissues: optic lobes, brain and ventral nerve cord. The flight muscle showed the presence of the message but in a lower amount. A much lower level of expression was found in: hindgut, silk gland, rectum, midgut and gonad. The 800 bp fragments represent the OA/TAT message amplified from cDNA and the 3 kb fragments represent the OA/TAT message amplified from genomic DNA present as a contaminant in RNA samples. In a similar way two different size products can be detected when two specific G3PDH primers were used. Detection of the G3PDH cDNA, a ubiquitous transcript served as an internal control for cDNA synthesis and PCR amplification. The 950 bp band is the G3PDH fragment amplified from cDNA and the weak band of 2.5 kb seen only in the RNA lane was amplified from the genomic DNA.

EXAMPLE 3

Expression and Pharmacological Characterization of Octopamine/Tyramine Transporter Expression Studies of the Cloned Octopamine/Tyramine Transporter cDNA For functional characterization of the OA/TAT protein, a complete copy of the OA/TAT ORF was assembled in one construct so that the resulting protein product could be expressed. To do so, the two primers 5'UTR and 3'UTR were used to PCR amplify the ORF from cDNA and clone the resulting product. The 2.2 kb DNA fragment encoding the complete ORF was then cloned into the baculovirus donor vector pFastBac1 behind the polyhedrin promoter. Transfer to baculovirus was accomplished by transposition using the Bac-to-Bac Baculovirus Expression System (Life Technologies). Insect cells were infected by the recombinant virus and the cells were assayed for TA/OAT activity.

Kinetics of Dopamine (DA) Uptake by Octopamine/Tyramine Transporter

Infection of insect cells with OA/TAT cDNA recombinant baculovirus induced the expression of OA/TAT indirectly visualized by the DA uptake activity of the cells, detected in the presence of 0.3 µM $^3$H-DA, 100 mM Na$^+$, 115 mM Cl$^-$. The uptake was linear for 4 min after which the rate started to decline. Consequently, all the kinetic and inhibition studies were done by measuring the $^3$H-DA uptake levels at 3 min, within linear range of uptake. The kinetic properties of OA/TAT for DA were determined from dose-dependent uptake of $^3$H-DA. Na$^+$ independent uptake of $^3$H-DA represented less than 10% of the Na$^+$ dependent uptake and all the data were corrected for the Na$^+$ independent uptake. The mean of apparent $K_m$ for DA is 2.9±0.4 µM (n=3) over a $V_{max}$ range of 5.1 to 17.8 pmoles/well/min, in three different experiments. Cells infected with a mock baculovirus, GUS (β-glucuronidase)-recombinant virus accumulated 3.32±0.28% of the $^3$H-DA accumulated in insect cells expressing OA/TAT.

Dopamine Uptake Inhibited by Potential Competitive Substrates or Inhibitors

Tyramine (TA), octopamine (OA) and norepinephrine (NE), naturally occurring monoamines that have a similar structure to DA, were tested together with DA for their ability to inhibit $^3$H-DA uptake. The concentration range of an unlabeled competitive inhibitor was selected according to the expected IC$_{50}$ value. The IC$_{50}$ values obtained were 0.39±0.11 µM for TA, 1.92±0.28 µM for OA, 4.10±1.02 µM for DA and 22.04±2.94 µM for NE. The apparent $K_i$ values (calculation based on Cheng et al., (1973) *Biochem Pharmacol* 22:3099) were 0.35±0.10 µM for TA, 1.74±0.25 µM for OA, 3.72±0.92 µM for DA and 20.04±2.67 µM for NE. The rank order of apparent $K_i$ on OA/TAT for potential substrates was: TA<OA<DA<NE.

The uptake of $^3$H-DA was also inhibited by other biogenic amines, their metabolites and other neurotransmitters, all tested at 10 µM (Table 1). Among the amines showing an inhibiting effect on $^3$H-DA uptake by OA/TAT uptake, (expressed as % inhibition at 10 µM), are: 2-phenylethylamine (61%), epinephrine (25%) and ephedrine (25%) (Table 1). The neurotransmitters tested serotonin and histamine, did not significantly alter the rate of $^3$H-DA uptake. Two tricyclic antidepressants, imipramine and desipramine, both used at 10 µM show inhibition effects of 50% and 73%, respectively (Table1). Nomifensine (10 µM), a selective antagonist for NET, inhibits 74% of control $^3$H-DA uptake. GBR 12909, a very potent and specific inhibitor of the mammalian DATs, did not affect OA/TAT's activity. Chlorpromazine (10 µM) a phenothiazine compound, inhibits the uptake 41% while Riluzole (100 µM) a competitive blocker of DAT did not influence the activity of OA/TAT (Table 1).

TABLE 1

Inhibition of $^3$H-Dopamine uptake by OA/TAT* by related phenylethylamines and other inhibitors of monoamine transport

| Compound | % Inhibition | SD |
| --- | --- | --- |
| Phenylethylamines and other monoamines | | |
| Tyramine | 96.54 | 0.90 |
| Octopamine | 80.89 | 0.69 |
| Dopamine | 70.18 | 6.46 |
| 2-Phenylethylamine | 60.98 | 1.05 |
| Norepinephrine | 27.23 | 6.67 |
| Epinephrine | 25.18 | 1.71 |

TABLE 1-continued

Inhibition of $^3$H-Dopamine uptake by OA/TAT* by related phenylethylamines and other inhibitors of monoamine transport

| Compound | % Inhibition | SD |
|---|---|---|
| Ephedrine | 24.88 | 3.87 |
| Synephrine | 6.39 | 7.39 |
| Pseudoephedrine | 1.31 | 3.94 |
| Tryptamine | 9.57 | 0.91 |
| Histamine | −1.81 | 1.78 |
| Serotonin | −3.6 | 3.70 |
| Drugs known to block monoamine transporters | | |
| Imipramine | 50.29 | 4.09 |
| Desipramine | 73.10 | 5.83 |
| Nomifensine | 74.08 | 2.33 |
| Chlorpromazine | 40.66 | 0.43 |
| GBR12909 | −10.04 | 12.99 |
| Riluzole** | −11.29 | 2.98 |

All data are the means of three experiments. SD represents standard deviation
*$^3$H-DA uptake by OA/TAT at 0.3 μM $^3$H-DA, 100 mM Na$^+$ and 115 mM Cl$^-$
**the inhibitor concentration used was 10 μM except for Riluzole (100 μM)

Na$^+$, Cl$^-$ Requirements for Octopamine/Tyramine Transporter Activity

Na$^+$ substitution with K$^+$, Li$^+$, choline$^+$ or NMG$^+$ in bathing saline reduced the DA uptake to between 2-4% of the control uptake (Na$^+$ 100 mM) indicating a strong requirement for Na$^+$. A previous study addressing the Cl$^-$ requirements of a related transporter, GABA transporter (TrnGAT-1) was performed in saline containing 100 mM Na$^+$ and 147.7 mM Cl$^-$ or their substitutes at the same concentration. The total amount of anions in these salines was 177.4 mM. Substitution studies using salines similar to those used for GABA transporter indicated that the anion requirements of OA/TAT is substantially different. Unlike for TrnGAT-1, salines containing Cl$^-$ or other anions at a concentration of 147.7 mM inhibited 90% of the OA/TAT activity. Thus, in the next set of salines the concentration of Cl$^-$ or other anions was lowered at 92.7 mM, supplementing the salines with SO$_4^{2-}$ (22.4 mM), H$_2$PO$_4^-$ (7.3 mM) and glutamate$^-$ (55 mM) to total anion concentration of 177.4 mM. The results using those salines showed that Br$^-$, NO$_3^-$, HPO$_4^{2-}$/H$_2$PO$_4^-$ and glutamate$^-$ were capable of sustaining 76%, 60%, 56% and 51% of OA/TAT activity in the absence of Cl$^-$. The rest of the salines containing gluconate$^-$, aspartate$^-$, I$^-$, citrate$^{3-}$ and SO$_4^{2-}$ sustained only 29%, 24%, 25%, 22% and 12% of the OA/TAT activity measured in the presence of Cl$^-$. Because every one of these salines contained low levels of SO$_4^{2-}$ (22.4 mM), H$_2$PO$_4^-$ (7.3 mM) and glutamate$^-$ (55 mM), a special saline containing only those anions was designed in order to detect the background uptake levels caused by their presence in every one of the salines. Surprisingly, this saline sustained 77% of the OA/TAT activity suggesting that one or more of the anions SO$_4^{2-}$, H$_2$PO$_4^-$, glutamate$^-$ or their combination could support the OA/TAT activity in the absence of Cl$^-$. To investigate this possibility more extensively, a final set of salines each containing a single anion species was designed (see Example 1).

The salines containing single anions were able to substitute for Cl$^-$ in supporting DA uptake as follows: H$_2$PO$_4^-$ (50 mM)(116%)>HPO$_4^{2-}$/H$_2$PO$_4^-$ (75 mM)(77%), CO$_3^{2-}$ (50 mM) (49%)>HCO$_3^-$/CO$_3^{2-}$ (75 mM)(45%) and glutamate$^-$ (100 mM)(27%). The rest of the salines at the concentrations tested did not significantly support the OA/TAT uptake. Also, the saline containing 100 mM Cl$^-$ by itself did not support the OA/TAT uptake. All the results were expressed as % control, where control is the $^3$H-DA uptake in the presence of Na$^+$ (100 mM), Cl$^-$ (92.7 mM), SO$_4^{2-}$ (22.4 mM), H$_2$PO$_4^-$ (7.3 mM) and glutamate$^-$ (55 mM).

EXAMPLE 4

Identification of Octopamine Transporter Sequences from Additional Species of Moth or Butterfly Partial octopamine transporter sequences (pOATs) have been obtained from seven species of moth or butterfly representing the seven major superfamilies within the higher Lepidoptera (the Ditrysia, which includes 98% of all moth species and all butterfly species). Nucleic acid sequences, shown in FIG. 2, were obtained by PCR using degenerate primers based on conserved regions of the full-length OAT from *Trichoplusia ni* (SEQ ID NO:1), the cabbage looper (fam. Noctuidae, superfam. Noctuidea). The area of the partial sequence represents about 23% of the full length *T. ni* cDNA, and includes a variable extracellular domain (ED2) but not the variable N- and C-termini. The partial nucleic acid sequence data contained in FIG. 2 suggests that the full-length cDNAs of the species listed in the legend of FIG. 2 will have slightly lower sequence identities than the partial sequences shown, i.e. a minimum of about 60% at the DNA level and about 80% at the protein levels.

Figure 4:
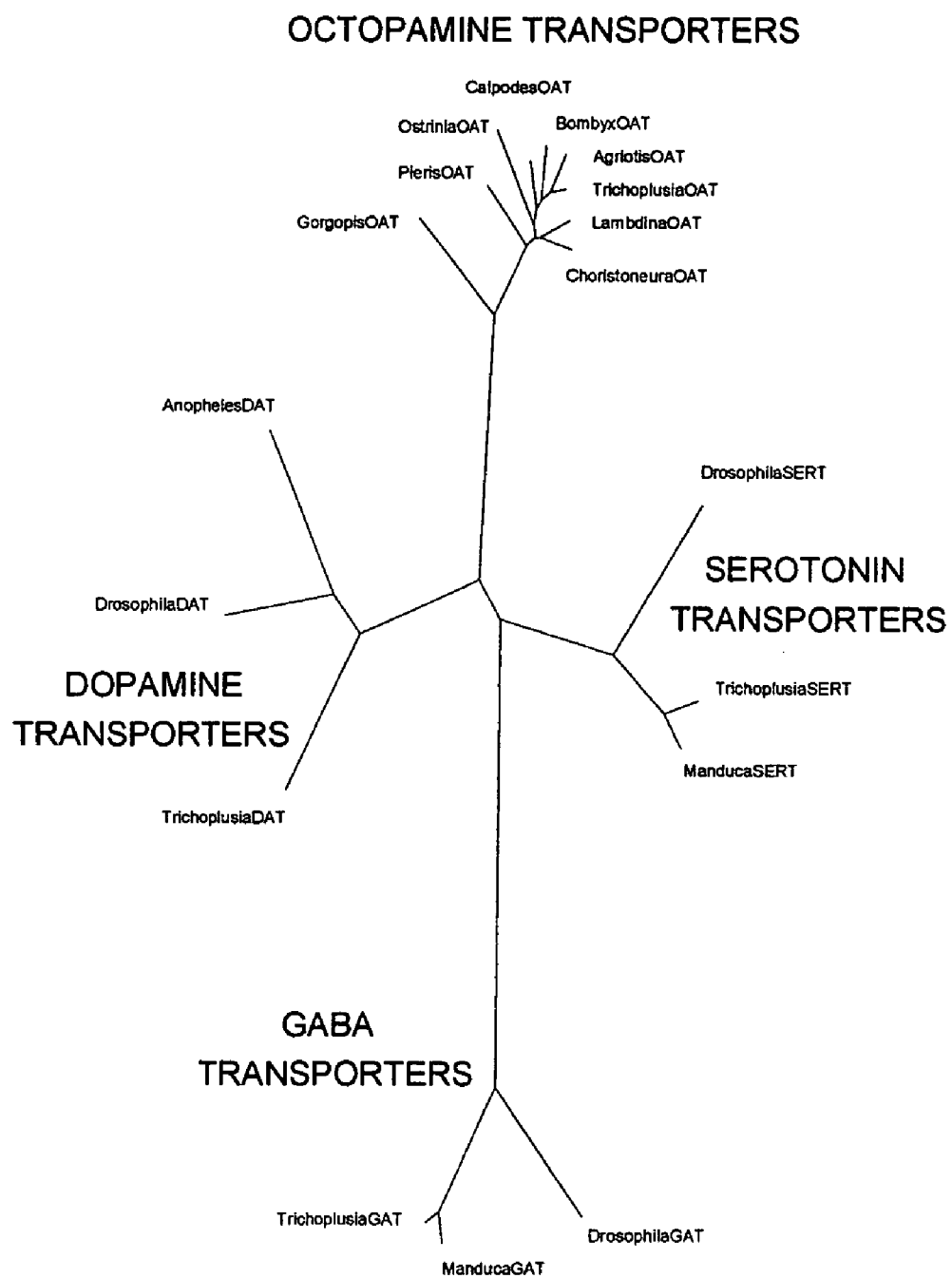
FIG. 4 depicts a phylogenetic tree derived from the nucleic acid sequence alignments depicted in FIG. 2 and an additional partial OAT sequence obtained from a primitive moth *Gorgopis libania* (Hepialidae, Hepialoidea), which has 63% sequence identity with *Trichoplusia*. These lepidopteran OATs are compared with characterized insect transporters for the neurotransmitters dopamine, GABA and serotonin, including the known lepidopteran sequences.

An alignment of the pOAT nucleic acid sequences as obtained using the Clustal W method is shown in FIG. 2, while the relative percent identities of these pOAT nucleic acid sequences are shown in FIG. 3. FIG. 4 depicts the genetic relationships between neurotransmitter (GABA, serotonin, dopamine and octopamine) transporters for various lepidopteran species. It is noteworthy that the octopamine transporter from the primitive moth *Gorgopis libania* (Hepialidae, Hepialoidea) is still fully functional despite having a sequence identity of only 63% at the nucleotide level relative to *Trichoplusia*.

Figure 5:
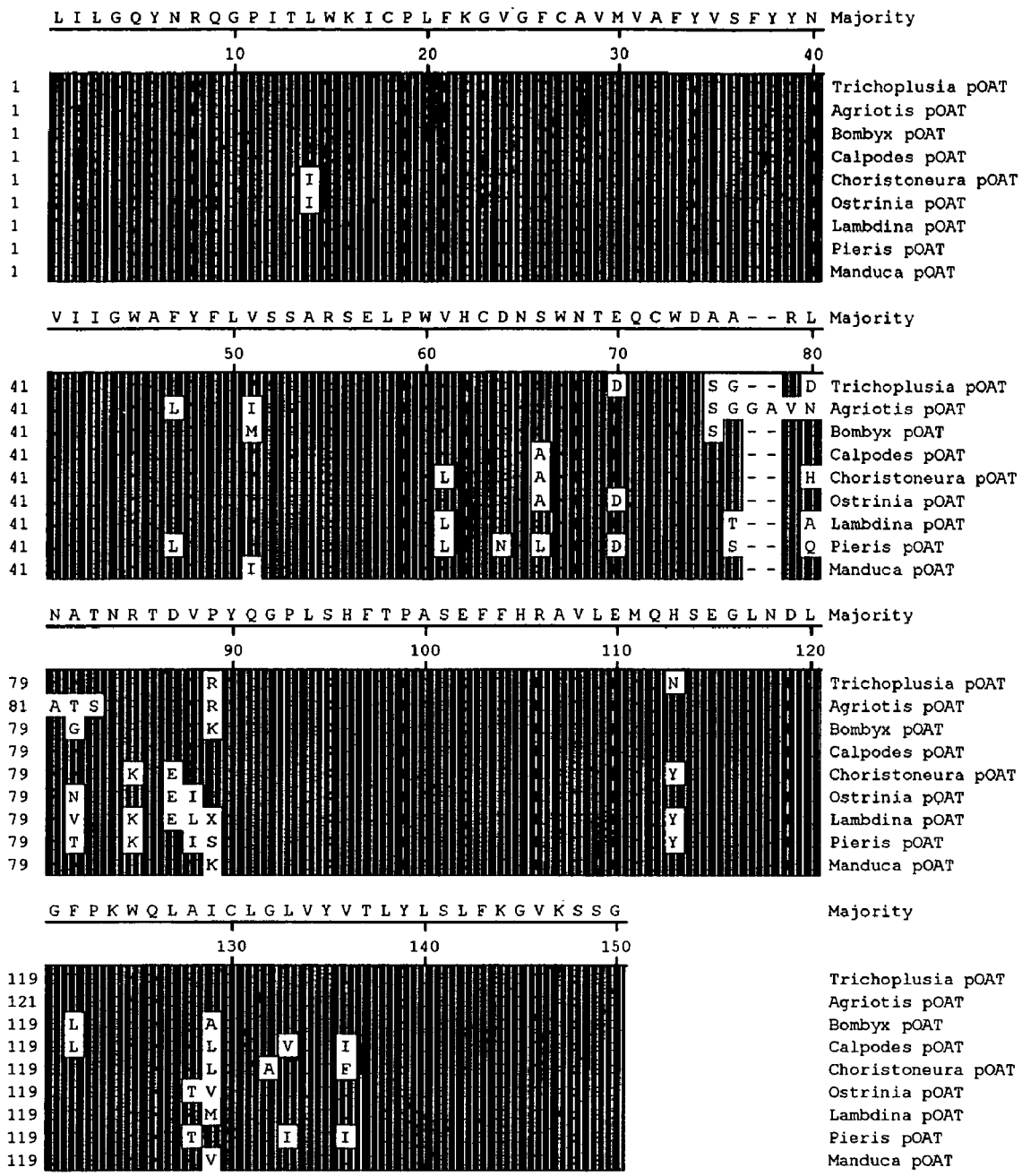
FIG. 5 depicts the alignment between partial octopamine transporter (pOAT) amino acid sequences obtained from eight species of moths or butterflies representing the seven major superfamilies within the higher Lepidoptera and that obtained from *Trichoplusia ni* (*Trichoplusia* pOAT). Abbreviations: *Agriotis*—black cutworm (*Agriotis epsilon*) of the superfamily Noctuoidea; *Bombyx*—silkmoth (*Bombyx mori*) of the superfamily Bombycoidea; *Calpodes*—Brazilian skipper (*Calpodes ethlius*) of the superfamily Hesperioidea; *Choristoneura*—Spruce budworm (*Choristoneura fumiferana*) of the superfamily Torticoidea; *Ostrinia*—cornborer (*Ostrinia nubilalis*) of the superfamily Pyraloidea; *Lambdina*—hemlock looper (*Lambdina fiscallaria*) of the superfamily Geometroidea; *Pieris*—cabbage white (*Pieris rapae*) of the superfamily Papilionoidea. *Manduca*—tomato hornworm (*Manduca cinquemaculata*) of the superfamily Bombycoidea. Majority: SEQ ID NO:31; *Trichoplusia*: SEQ ID NO:32; *Agriotis*: SEQ ID NO:33; *Bombyx*: SEQ ID NO:34; *Calpodes*: SEQ ID NO:35; *Choristoneura*: SEQ ID NO:36; *Ostrinia*: SEQ ID NO:37; *Lamdina*: SEQ ID NO:38; *Pieris*: SEQ ID NO:39; *Manduca*: SEQ ID NO:40.

An alignment, also obtained using the Clustal W method, of the pOAT amino acid sequences that correspond to the nucleic acid sequences depicted in FIG. 2 is shown in FIG. 5. The relative percent identities of these pOAT amino acid sequences are shown in FIG. 6.

We claim:

1. An isolated nucleic acid encoding a lepidopteran octopamine/tyramine transporter that hybridizes under moderate stringency conditions to the complement of a nucleic acid having the nucleotide sequence of SEQ ID NO:1, said isolated nucleic acid having at least about 70% sequence identity to the nucleic acid having the nucleotide sequence of SEQ ID NO: 1, and wherein the lepidopteran octopamine/tyramine transporter encoded by said isolated nucleic acid has sodium-dependent transport activity which has affinity for dopamine and which is inhibited by octopamine and tyramine.

2. The isolated nucleic acid of claim 1 having at least about 75% sequence identity to the nucleic acid having the nucleotide sequence of SEQ ID NO: 1.

3. A vector comprising the nucleic acid of claim 1 operably linked to a promoter.

4. The vector of claim 3 wherein the vector is a baculovirus vector.

5. A host cell comprising the vector of claim 4.

6. The host cell of claim 5 wherein the cell is an insect cell.

7. The host cell of claim 6 wherein the cell is *Spodoptera frugiperda*.

* * * * *